US008624013B2

(12) United States Patent
Presta

(10) Patent No.: US 8,624,013 B2
(45) Date of Patent: Jan. 7, 2014

(54) INTERLEUKIN-10 ANTIBODIES

(75) Inventor: Leonard G. Presta, San Francisco, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/553,554

(22) Filed: Jul. 19, 2012

(65) Prior Publication Data

US 2012/0282253 A1 Nov. 8, 2012

Related U.S. Application Data

(60) Division of application No. 12/701,386, filed on Feb. 5, 2010, now Pat. No. 8,226,947, which is a division of application No. 11/623,006, filed on Jan. 12, 2007, now Pat. No. 7,662,379, which is a continuation of application No. 10/985,584, filed on Nov. 9, 2004, now abandoned.

(60) Provisional application No. 60/518,999, filed on Nov. 10, 2003.

(51) Int. Cl.
*C07H 21/04* (2006.01)

(52) U.S. Cl.
USPC ...................................... 536/23.53; 435/326

(58) Field of Classification Search
None
See application file for complete search history.

(56) References Cited

U.S. PATENT DOCUMENTS

| 5,585,089 A | 12/1996 | Queen et al. |
| 6,407,213 B1 | 6/2002 | Carter et al. |
| 7,148,038 B2 | 12/2006 | Mather |
| 2002/0039581 A1 | 4/2002 | Carreno et al. |
| 2003/0039649 A1 | 2/2003 | Foote |
| 2003/0108966 A1 | 6/2003 | Mather |

FOREIGN PATENT DOCUMENTS

| DE | 195 29 026 A1 | 1/1997 |
| EP | 0 541 214 A2 | 5/1993 |
| WO | WO 94/04180 A2 | 3/1994 |
| WO | WO 02/46237 A2 | 6/2002 |
| WO | WO 03/085089 A2 | 10/2003 |

OTHER PUBLICATIONS

Abrams et al. (1992) *Immunol rev.* 127:5-24, "Strategies of Anti-Cytokine Monoclonal Antibody Development: Immunoassay of IL-10 and IL-5 in Clinical Samples".
Beebe et al. (2002) *Cytokine & Growth Factor Reviews* 13:403-412, "The role of interleukin-10 in autoimmune desease: systemic lupus erythematosus (SLE) and multiple sclerosis (MS)".
Brady et al. (2003) *Eur. J. Immunol.* 33:3448-3457, "Hepatitis C virus non-structural protein 4 suppresses Th1 responses by stimulating IL-10 production from monocytes".
Caldas et al. (2003) *Molecular Immunol.* 39:941-952, "Humanization of the anti-CD18 antibody 6.7: an unexpected effect of a framework residue in binding to antigen".
Caldas et al. (2000) *Protein Engineering* 13(5):353-360 "Design and synthesis of germline-based hemi-humanized single-chain Fv against the CD18 surface antigen".
Clerici et al., *J. Clin. Invest.* (Feb. 1994) 93:768-775 "Role of Interleukin-10 in T Helper Cell Dysfunction in Asymptomatic Individuals Infected with the Human Immunodeficiency Virus".
D'Andrea et al., *J. Exp. Med.* (1993) 178:1041-1048 "Interleukin 10 (IL-10) Inhibits Human Lymphocyte Interferon γ-Production by Suppressing Natural Killer Cell Stimulatory Factor/IL-12 Synthesis in Accessory Cells".
DeWaal Malefyt et al., *J. Exp. Med.* (1991) 174:915-924 "Interleukin 10 (IL-10) and Viral IL-10 Strongly Reduce Antigen-specific Human T Cell Proliferation by Diminishing the Antigen-presenting Capacity of Monocytes via Downregulation of Class II Major Histocompatibility Complex Expression".
Fiorentino et al., *J. Exp. Med.* (1989) 170:2081-2095 "Two Types of Mouse T Helper Cell, IV. Th2 Clones Secrete a Factor that Inhibits Cytokine Production by Th1 Clones".
Fiorentino et al., *J. Immunol.* (1991) 146:3444-3451 "IL-10 Acts on the Antigen-Presenting Cell to Inhibit Cytokine Production by Th1 Cells".
Fiorentino et al., *J. Immunol.* (1991) 147:3815-3822 "IL-10 Inhibits Cytokine Production by Activated Macrophages".
Gonzalez-Amaro, et al. *J. Autoimmunity* (1998) 11:395-402 "Role of IL-10 in the Abnormalities of Early Cell Activation Events of Lymphocytes from Patients with Systemic Lupus Erythematosus".
Heinrichs et al. (1995) *J. Immunol. Methods* 178(2):241-251 "Universal cloning and direct sequencing of rearranged antibody V genes using C region primers, biotin-captured cDNA and one-side PCR".
Hsu et al., *Int. Immunol.* (1992) 4:563-569 "Differential effects of IL-4 and IL-10 on IL-2-induced IFN-γ synthesis and lymphokine-activated killer activity".
Huang, et al., *Mol. Immunol.* (1997) 34(18):1291-1301 "Variable Domain Structure of κIV Human Ligth Chain Len: High Homology to the Murine Light Chain McPC603".
Hudson, et al. (2003) *Nature Medicine* 9(1):129-134 "Engineered Antibodies".
Illei and Czirják *Expert Opin. Investig. Drugs* (2001) 10(6):1117-1130 "Novel Approaches in the Treatment of Lupus Nephritis".
Ishida, H., *Medical Immunology* (1991) 21(5):625-629, Japanese Publication (English Translation), "Interleukin 10".
Janeway et al. *Immunobiology*, 5th Ed., Garland Science, pp. 100-105 (2001).
Lin et al. (1996) *Infect. Immun.* 64(4):1351-1356 "Absence of a Prominent Th2 Cytokine Response in Human Tuberculosis".
Llorente et al. *Arthritis Rheum.* Aug. 2000;43(8):1790-800 "Clinical and Biologic Effects of Anti-Interleukin-10 Monoclonal Antibody Administration in Systemic Lupus Erythematosus".
Ma, Xiaojing, et al. (2000) *J. of Immunol.* 164(4):1722-1729 "Inhibition of IL-12 production in human monocyte-derived macrophages by TNF".
Merluzzi, et al. (2000) *Advances in Clinical Pathology* 4(2):77-85 "Humanized antibodies as potential drugs for therapeutic use".
Moore et al., *Annu. Rev. Immunol.* (1993) 11:165-190 "Interleukin-10".

(Continued)

*Primary Examiner* — Zachary Skelding
(74) *Attorney, Agent, or Firm* — Sheela Mohan-Peterson

(57) ABSTRACT

The methods and compositions provided herein relate generally to IL-10 specific antibodies and uses thereof. More specifically, compositions of humanized IL-10 specific antibodies and methods to use such antibodies in modulating the biological activity of IL-10, particularly in autoimmune disorders and pathogen-mediated immunopathology.

7 Claims, 10 Drawing Sheets

(56) References Cited

OTHER PUBLICATIONS

Pavlinkova et al., *Cancer Immunol Immunother.* (2000) 49:267-275. "Pharmacokinetics and biodistribution of a light-chain-shuffled CC49 single-chain Fv antibody construct".

Pluschke et al., *J. Immunol. Methods* (1998) 215:27-37 "Generation of chimeric monoclonal antibodies from mice that carry human immunoglobulin Cγ1 heavy of Cκ light chain gene segments".

Portolano et al. (1993) *J. Immunol.* 150(3):880-887 "Lack of Promiscuity in Autoantigen-Specific H and L Chain Combinations as Revealed by Human H and L Chain 'Roulette'".

Schroeder et al. (1990) *Proc. Natl. Acad. Sci. USA* 87(16):6146-6150 "Preferential utilization of conserved immunoglobulin heavy chain variable gene segments during human fetal life".

Takai et al. *Int. Arch. Allergy Immunol.* (2000) 123:308-318 "Inhibition of IgE-Dependent Histamine Release from Human Peripheral Blood Basophils by Humanized Fab Fragments That Recognize the Membrane Proximal Domain of the Human FcεRI α-Chain".

Tan et al. *J. Immunology* (2002) 169:1119-1125 "Superhumanized Antibodies: Reduction of Immunogenic Potential by Complementarity-Determining Region Grafting with Human Germline Sequences: Application to an Anti-CD28".

Wu et al. (1999) *J. Mol. Biol.* 294:151-162."Humanization of a Murine Monoclonal Antibody by Simultaneous Optimization of Framework and CDR Residues".

FIGURE 1A

| 12G8 VL sequence | = Affects CDR (Chothia et al.) | ^ = Affects CDR | = Interface |

VLK I

```
              10         20         30              40         50         60         70         80         90
12G8   DIQMTQSPSLLSASVGDRVTLNC KTSQNIF------ENLA WYQQKLREPPKLLIF NASPLQA GIPSRFSGSGSGTDFTLTITSLQPEDVATYFC HQYYSGY
47      4 3                                4            2 2     2 234              1 111 1 111111 1111 111111 111 1
47     1 1 11111 1111111111   1                         1 1 1     1
Z-O12  DIQMTQSPSLLSASVGDRVTITC RASQSIS-----SYLN WYQQKPGKAPKLLIY AASSLQS GVPSRFSGSGSGTDFTLTISSLQPEDFATYYC QQSYSTP
              ^                              ^            ^             ^                                   ^
```

VLK II

```
              10         20         30              40         50         60         70         80         90
12G8   DIQMTQSPSLLSASVGDRVTLNC KTSQNIF------ENLA WYQQKLREPPKLLIF NASPLQA GIPSRFSGSGSGTDFTLTITSLQPEDVATYFC HQYYSGY
40      4 3                              4              2 2     2 234              2 4                                     4
28     1 1111 1    1      1               1            1 1     1
Z-A19  DIVMTQSPLSLPVTPGEPASISC RSSQSLLHS-NGYNYLD WYLQKPGQSPQLLIY LGSNRAS GVPDRFSGSSGSGTDFTLKISRVEAEDVGVYYC MQALQTP
              ^                              ^            ^             ^                                   ^
```

VLK III

```
              10         20         30              40         50         60         70         80         90
12G8   DIQMTQSPSLLSASVGDRVTLNC KTSQNIF------ENLA WYQQKLREPPKLLIF NASPLQA GIPSRFSGSGSGTDFTLTITSLQPEDVATYFC HQYYSGY
45      4                                42              2 2     2 234              3 3 4                                 42
36     1111  11 1 1 1111 11 1                         1 1 1     1          1 1 1 111111 1111 1 111 1 1 1
Z-A27  EIVLTQSPGTLSLSPGERATLSC RASQSVSSSYLA WYQQKPGQAPRLLIY GASSRAT GIPDRFSGSGSGTDFTLTISRLEPEDFAVYYC QQYGSSP
              ^                              ^            ^             ^                                   ^
```

VLK IV

```
              10         20         30              40         50         60         70         80         90
12G8   DIQMTQSPSLLSASVGDRVTLNC KTSQNIF------ENLA WYQQKLREPPKLLIF NASPLQA GIPSRFSGSGSGTDFTLTITSLQPEDVATYFC HQYYSGY
47      4 3                                                     42  2 2    22 234              3 4                         42
39     1 1111 1  1 1 1 1 11                                     1 1 1     1
Z-B3   DIVMTQSPDSLAVSLGERATINC KSSQSVLYSSNNKNYLA WYQQKPGQPPKLLIY WASTRES GVPDRFSGSGSGTDFTLTISSLQAEDVAVYYC QQYYSTP
              ^                              ^            ^             ^                                   ^
```

FIGURE 1B

```
                      = Affects CDR (Chothia et al.)   ^ = Affects CDR   = Interface 12G8 VH sequence VH1
Kabat protein consensus
humI    QVQLVQSGAEVKKPGASVKVSCKAS GYTFTSYAIS  WVRQAPGQGLEWMG WINPNGNGDTNYAQKFQG RVTITADTSTSTAYMELSSLRSEDTAVYYCAR
                 10        20         26                40         50       60          70        80  abc      90
DP-14   QVQLVQSGAEVKKPGASVKVSCKAS GYTFTSYGIS  WVRQAPGQGLEWMG WISAYNGNTNYAQKLQG RVTIMTTDTSTSTAYMELRSLRSDDTAVYYCAR
        42                       3   44       2 2  22 4     3                1 1          1 1     1111 111   2 4
        26       1 1 1 11       11 1   1      1 1  1 1                                                       1
12G8    EVQLVESGGGLVRPGGSLRLSCTAS GFTFSDYHMA  WVRQSPDKGLEWVA SITLDATYTYRDSVRG RFTISRNNAKTTLYLQMDSLRSEDTATFYCTR
                ^                  ^          ^^ ^            ^^^^^  ^ ^^^     ^    ^ ^^        ^

VH3
Kabat protein consensus
humIII  EVQLLESGGGLVQPGGSLRLSCAAS GFTFSSYAMS  WVRQAPGKGLEWVS VISGDGGSTYYADSVKG RFTISRDNSKNTLYLQMNSLRAEDTAVYYCAR
                 10        20         26                40         50       60          70        80  abc      90
DP-47   EVQLLESGGGLVQPGGSLRLSCAAS GFTFSSYAMS  WVRQAPGKGLEWVS AISGSGSTYYADSVKG RFTISRDNSKNTLYLQMNSLRAEDTAVYYCAK
        70                       3   44 4     2 2  22 43     3                3 3 3 3         3                 2
        41       1 1111111 111111111 1   1    1 1  1 1 1                      1 1 1  1 1 1111 111 1111          1
12G8    EVQLVESGGGLVRPGGSLRLSCTAS GFTFSDYHMA  WVRQSPDKGLEWVA SITLDATYTYRDSVRG RFTISRNNAKTTLYLQMDSLRSEDTATFYCTR
                ^                  ^          ^^ ^            ^^^^^  ^ ^^^     ^    ^ ^^        ^

DP-46   QVQLVESGGGVVQPGRSLRLSCAAS GFTFSSYAMH  WVRQAPGKGLEWVA VISYDGSNKYYADSVKG RFTISRDNSKNTLYLQMNSLRAEDTAVYYCAR
        77                       3   44 4     2 2  22 433    3                3 3 3 3         3                 2 4
        39       1 1111111 1 11 111111 1 1    1 1  1 1 1                      1 1 1  1 1 1111 111 1111          1
12G8    EVQLVESGGGLVRPGGSLRLSCTAS GFTFSDYHMA  WVRQSPDKGLEWVA SITLDATYTYRDSVRG RFTISRNNAKTTLYLQMDSLRSEDTATFYCTR
                ^                  ^          ^^ ^            ^^^^^  ^ ^^^     ^    ^ ^^        ^

DP-58   EVQLVESGGGLVQPGGSLRLSCAAS GFTFSSYEMN  WVRQAPGKGLEWVS YISSSGSTIYYADSVKG RFTISRDNAKNSLYLQMNSLRAEDTAVYYCAR
        74                       3   44 4     2 2  22 43     3                3 3 3 3         3                 2 4
        42       1 1111111 1111111 1 1   1    1 1  1 1 1                      1 1  11   1111 111 1111           1
12G8    EVQLVESGGGLVRPGGSLRLSCTAS GFTFSDYHMA  WVRQSPDKGLEWVA SITLDATYTYRDSVRG RFTISRNNAKTTLYLQMDSLRSEDTATFYCTR
                ^                  ^          ^^ ^            ^^^^^  ^ ^^^     ^    ^ ^^        ^
```

FIGURE 1B (continued)

```
VH4
Kabat protein consensus
humII  QVQLQESGPGLVKPSQTLSLTCTVS GGSVSS-YWS   WIRQPPGKGLEWIG RIY-YSGSTxYNPSLKS RVTISVDTSKNQFSLKLSSVTAADTAVYYCAR
              10        20       26                40        50       60           70       80  abc    90
DP-71  QVQLQESGPGLVKPSETLSLTCTVS GGSISSYYWS   WIRQPPGKGLEWIG YIY-YSGSTNYNPSLKS RVTISVDTSKNQFSLKLSSVTAADTAVYYCAR
35             4                                      3                         3                            2 4
28     1   111 111 1     1 1 11 1             2  22 4     1                2    1 1 1  1  1  1   111  1
                                              1  1  1 1 1
12G8   EVQLVESGGGLVRPGGSLRLSCTAS GFTFSDYHMA   WVRQSPDKGLEWVA SITLDATYTYYRDSVRG RFTISRNNAKTLYLQMDSLRSEDTATFYCTR
              ^                                  ^ ^ ^            ^ ^ ^ ^ ^              ^
```

FIGURE 1C

```
11D8 VL sequence       = Affects CDR (Chothia et al.)    ^ = Affects CDR    = Interface 10         20         30         40         50         60         70         80         90
VLK I
11D8   DIVLTQSPASLAVSLGQRATISC RASESVDDYDYGHSFMH       WYQQKPGQPPKLLIW RASTLES GIPARFSGSGSRTDFTLTINPVEADDVATYYC QQGNEDP
48         4                       4                  2 2     2 434                3    4                              2   24  4
37     1   1111 11   1   1 111 11   1                 1 1 111     1                1 1 1 111 11 11 1111               1 111 1
Z-O12  DIQMTQSPSSLSASVGDRVTITC RASQSIS----SYLN         WYQQKPGKAPKLLIY AASSLQS GVPSRFSGSGSGTDFTLTISSLQPEDFATYYC QQSYSTP
           ^                       ^                  ^                ^                                              ^

VLK II
11D8   DIVLTQSPASLAVSLGQRATISC RASESVDDY---GHSFMH      WYQQKPGQPPKLLIW RASTLES GIPARFSGSGSRTDFTLTINPVEADDVATYYC QQGNEDP
42         4                       4                  2 2     2 434                3    4                              2   24  4
38     1 1 1111 11   1   1 111                        1   1111        1            1 1 1 111 111 11   1 111 11  1 1     1 111 1
Z-A19  DIVMTQSPLSLPVTPGEPASISC RSSQSLLHS-NGYNYLD       WYLQKPGQSPQLLIY LGSNRAS GVPDRFSGSGSGTDFTLKISRVEAEDVGVYYC MQALQTP
           ^                       ^                  ^                ^                                              ^

VLK III
11D8   DIVLTQSPASLAVSLGQRATISC RASESVDDYDYGHSFMH       WYQQKPGQPPKLLIW RASTLES GIPARFSGSGSRTDFTLTINPVEADDVATYYC QQGNEDP
58         4                       4                  2 2     2 434              3  3    4                              2   24  4
37     1   1111  1   1   1 111 11                     1 1 1111                    1 1 1 111 11 11 1111               1 1111 1
Z-A27  EIVLTQSGTLSLSPGERATLSC  RASQSVSS----SYLA        WYQQKPGQAPRLLIY GASSRAT GIPDRFSGSGSGTDFTLTISRLEPEDFAVYYC QQYGSSP
           ^                       ^                  ^                ^                                              ^

VLK IV
11D8   DIVLTQSPASLAVSLGQRATISC RASESVDDYDYGHS--FMH     WYQQKPGQPPKLLIW RASTLES GIPARFSGSGSRTDFTLTINPVEADDVATYYC QQGNEDP
52         4                       4                  2 2    22 434                3    4                              2   24  4
44     1 1 1111 1111111  1111 1                       1 1 1111                     1 1 1 111 11 1111 1111          1 111 11
Z-B3   DIVMTQSPDSLAVSLGERATINC KSSQSVLYSSNNKNYLA       WYQQKPGQPPKLLIY WASTRES GVPDRFSGSGSGTDFTLTISSLQAEDVAVYYC QQYYSTP
           ^                       ^                  ^                ^                                              ^
```

FIGURE 1D

```
11D8 VH sequence        = Affects CDR (Chothia et al.)   ^ = Affects CDR    = Interface VH1
Kabat protein consensus
humI     QVQLVQSGAEVKKPGASVKVSCKAS GYTFTSYAIS WVRQAPGQGLEWMG WINPGNGDTNYAQKFQG RVTITADTSTSTAYMELSSLRSEDTAVYYCAR
                 10        20         26                   40         50          60                70           80 abc  90
DP-14    QVQLVQSGAEVKKPGASVKVSCKAS GYTFTSYGIS WVRQAPGQGLEWMG WISAYNGNTNYAQKLQG RVIMTTDTSTSTAYMELRSLRSDDTAVYYCAR
         4 3                       4          2 2  22 4 3  3                  3                                 2 34
         1 1 111                   1 1        1 1 11       3                  1        3                  11   111 1 1
11D8     QVQLKQSGPGLVQPSQSLSITCTVS GFSLTNYGVH WVRQSPGKGLEWLG VIW-SGGSTDYNAAFIS RLSINKDNSKSQVFFKMNSLQANDTAIYYCAR
         ^                         ^          ^^ ^          ^ ^ ^ ^ ^ ^                                    ^

VH3
Kabat protein consensus
humIII   EVQLVESGGGLVQPGGSLRLSCAAS GFTFSSYAMS WVRQAPGKGLEWVS VISGDGSTYYADSVKG RFTISRDNSKNTLYLQMNSLRAEDTAVYYCAK
                 10        20         26                   40         50         60                70           80 abc  90
DP-47    EVQLLESGGGLVQPGGSLRLSCAAS GFTFSSYAMS WVRQAPGKGLEWVS AISGSGGSTYYADSVKG RFTISRDNSKNTLYLQMNSLRAEDTAVYYCAK
         4 3                       44         2 2  22 4     3                 3  3                              2 3
         1  11 11111 11  1  1       1 1        1 111  1           1    11      1   1 11        1111 1 111 1 1
11D8     QVQLKQSGPGLVQPSQSLSITCTVS GFSLTNYGVH WVRQSPGKGLEWLG VIW-SGGSTDYNAAFIS RLSINKDNSKSQVFFKMNSLQANDTAIYYCAR
         ^                         ^          ^^ ^          ^                  ^                               ^

DP-46    QVQLVESGGGVVQPGRSLRLSCAAS GFTFSSYAMH WVRQAPGKGLEWVA VISYDGSNKYYADSVKG RFTISRDNSKNTLYLQMNSLRAEDTAVYYCAR
         4 3                       44       2 2  22 4       23                3  3                              2 34
         1 1  11 1 111  11  1  1    1 1      1 111  1             1    11      1   1 11        1111 1 111 1 1
11D8     QVQLKQSGPGLVQPSQSLSITCTVS GFSLTNYGVH WVRQSPGKGLEWLG VIW-SGGSTDYNAAFIS RLSINKDNSKSQVFFKMNSLQANDTAIYYCAR
         ^                         ^          ^^ ^          ^                  ^                               ^

DP-58    EVQLVESGGGLVQPGGSLRLSCAAS GFTFSSYDMN WVRQAPGKGLEWVS YISSSGSTIYYADSVKG RFTISRDNAKNSLYLQMNSLRAEDTAVYYCAR
         4 3                       44         2 2  22 4     3                 3  3                              2 34
         1  11 11111 11  1  1       1 1        1 111  1             1    1      1    1 1        1111 1 111 1 1
11D8     QVQLKQSGPGLVQPSQSLSITCTVS GFSLTNYGVH WVRQSPGKGLEWLG VIW-SGGSTDYNAAFIS RLSINKDNSKSQVFFKMNSLQANDTAIYYCAR
         ^                         ^          ^^ ^          ^                  ^                               ^
```

FIGURE 1D (continued)

```
VH4
Kabat protein consensus
humII  QVQLQESGPGLVKPSQTLSLTCTVS GGSVSS--YWS  WIRQPPGKGLEWIG RIYYSGSTxYNPSLKS  RVTISVDTSKNQFSLKLSSVTAADTAVYYCAR
                10        20        26                    40        50        60                70        80  abc   90
DP-71  QVQLQESGPGLVKPSETLSLTCTVS GGSISSYYWS   WIRQPPGKGLEWIG YIYYSGSTNYNPSLKS  RVTISVDTSKNQFSLKLSSVTAADTAVYYCAR
47         4 3                   3  4                 2   22 4 3   3        32                3                           2 34
35     1 1    111111 11   11 111 1          1 1 111 1                                       1    1 111 1  1   1 111 11    1 1
11D8   QVQLKQSGPGLVQPSQSLSITCTVS GFSLTNYGVH   WVRQSPGKGLEWLG VIWSGGSTDYNAAFIS  RLSINKDNSKSQVFFKMNSLQANDTAIYYCAR
           ^                              ^                 ^^  ^          ^^  ^^                                 ^
```

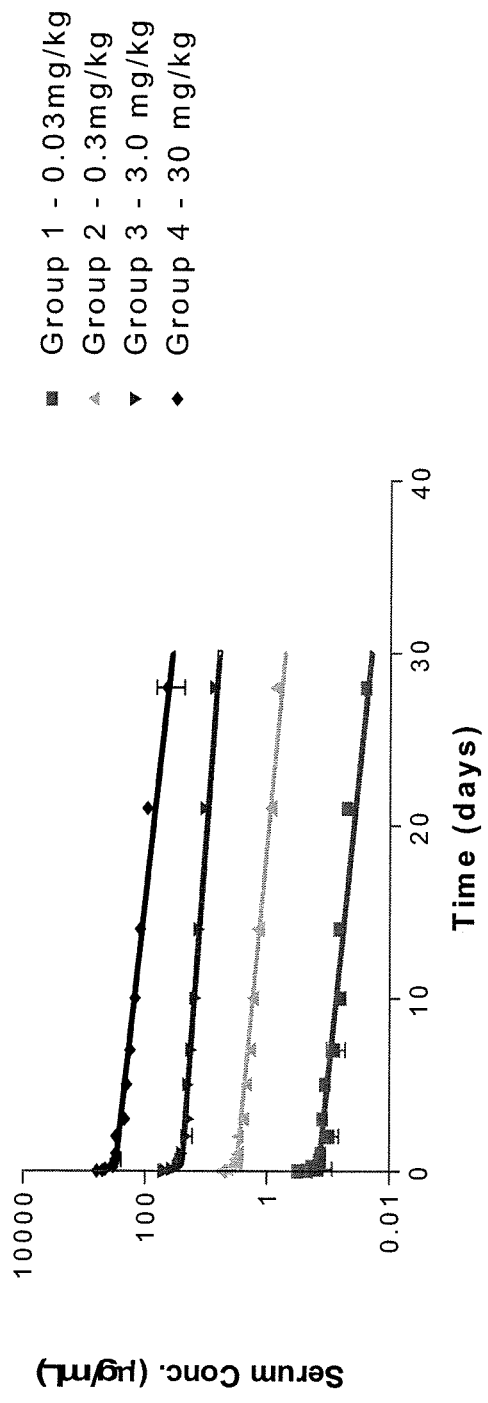
Figure 2A. Concentration-time profiles following intravenous bolus administration of 0.03 mg/kg – 30 mg/kg

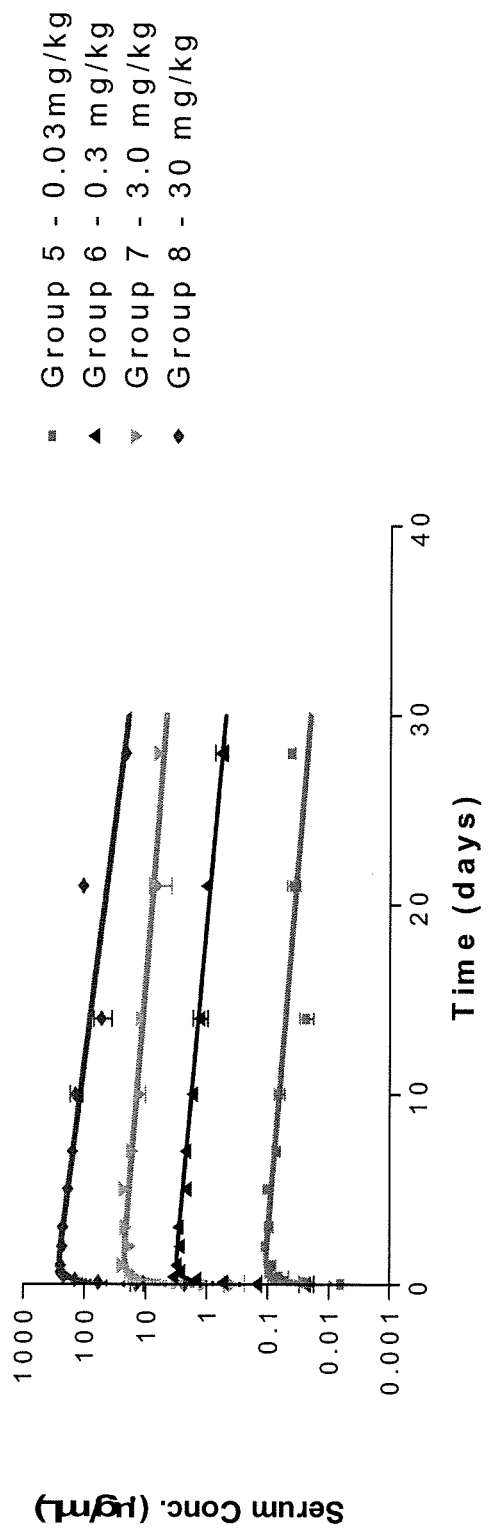
Figure 2B. Concentration-time profiles following subcutaneous bolus administration of 0.03 mg/kg – 30 mg/kg

INTERLEUKIN-10 ANTIBODIES

This application is a Divisional of U.S. patent application Ser. No. 12/701,386, filed on Feb. 5, 2010, which is a Divisional of U.S. patent application Ser. No. 11/623,006, filed on Jan. 12, 2007, now U.S. Pat. No. 7,662,379, issued on Feb. 16, 2010, which is a Continuation of U.S. patent application Ser. No. 10/985,584, filed Nov. 9, 2004, now abandoned, which claims benefit from U.S. Provisional Patent Application No. 60/518,999, filed Nov. 10, 2003, each of which is incorporated herein by reference in its entirety.

The Sequence Listing filed electronically herewith is also hereby incorporated by reference in its entirety (File Name: DX06061-US-DIV_SeqListing.txt; Date Created: Jul. 17, 2012; File Size: 39.6 KB.)

FIELD OF THE INVENTION

The present invention relates generally to interleukin-10 (IL-10) specific antibodies and uses thereof. More specifically, the invention relates to humanized antibodies that recognize human IL-10 and modulate its activity, particularly in autoimmune disorders.

BACKGROUND OF THE INVENTION

Initially known as cytokine synthesis inhibitor factor or CSIF, interleukin-10 (IL-10) is a potent immunomodulator of hematopoietic cells, particularly immune cells. Cells such as activated Th2 cells, B cells, keratinocytes, monocytes and macrophages produce IL-10. See, e.g., Moore et al., *Annu. Rev. Immunol.* 11:165 (1993). IL-10 inhibits activation and effector functions of a number of cells that include T cells, monocytes and macrophages. In particular, IL-10 inhibits cytokine synthesis, including that of IL-1, IFN-γ, and TNF, by cells such as Th1 cells, natural killer cells, monocytes, and macrophages. See, e.g., Fiorentino et al., *J. Exp. Med.*, 170: 2081-2095 (1989); Fiorentino et al., *J. Immunol.* 146:3444 (1991); Hsu et al., *Int. Immunol.* 4:563 (1992); Hsu et al., *Int. Immunol.* 4:563 (1992); D'Andrea et al., *J. Exp. Med.* 178: 1041 (1993); de Waal Malefyt et al., *J. Exp. Med.* 174:915 (1991); Fiorentino et al., *J. Immunol.* 147:3815 (1991).

Multiple pathogens, particularly intracellular pathogens, elicit IL-10 production to slow or completely stall the effective removal of the pathogen by the immune response. Moore et al., *Annu. Rev. Immunol.* 11:165 (1993). For example, in blood lymphocytes from patients with HIV, leprosy, or tuberculosis, peripheral blood lymphocytes are typically anergic or nonresponsive in vitro when challenged with the pathogen. However, the neutralization of IL-10 in these demonstrated that an active effector response, i.e., Th1 reactivity, was present in these cells. Thus, it is believed that IL-10 is effectively commandeered by the pathogen to facilitate its infective state.

IL-10 is also associated with autoimmunity in vivo. Autoimmunity results from the development from autoantibodies, autoreactive T cells, or some combination thereof that target normal tissue. One example of autoimmune disease is systemic lupus erythematosus (SLE), a chronic rheumatic disease in which connective tissue throughout the body becomes inflamed. Autoantibodies that attack normal body tissue as if it were an outside invade result in the characteristic inflammation. While the precise cause is not fully understood, researchers believe it has both genetic and environmental components. Specifically, B-cell hyperactivity and the presence of various autoantibodies characterize SLE. Typically, IgG autoantibodies reactive to double stranded DNA (IgG anti-dsDNA abs) are elevated in patients with SLE. Between 60 and 70% of SLE patients produce IgG anti-dsDNA abs, some of which are nephrotoxic. SLE is ten times more prevalent in women than men, with symptoms ranging from facial rashes to disabling and potentially life-threatening organ dysfunction. It can develop at any age, but is most common in young adults.

Numerous studies support a role for IL-10 in the pathology associated with SLE. For example, while IL-10 is typically not produced by cells without appropriate stimulation, both B cells and macrophages from SLE patients spontaneously produce high levels of IL-10 in vitro. Llorente, et al., *Arthritis Rheum.* 40:249-60 (1997). In several studies, researchers demonstrated a correlation between serum levels of IL-10 and disease activity. Moreover, both in vivo and in vitro studies demonstrated that the blockade of IL-10 production can alleviate the clinical manifestations of SLE. See, e.g., Gonzalez-Amaro, et al. *J. Autoimmunity* 11:395-402 (1998).

To date, one of the manifestations of SLE, lupus nephritis, has been treated with through the use of immunosuppressive therapies, e.g., corticosteriods and cyclophosphamides. Although effective, these therapies are non-specific and substantial toxicities exist which prevent long term therapy. Thus, specific neutralizing antibodies may be effective antagonists of IL-10, permitting the removal of the suppressive effects of IL-10 while leaving the remainder of the immune response network intact.

The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al., *Proc. Natl. Acad. Sci. USA* 84:3439 (1987). However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al., *Nature* 321:522 (1986); Verhoeyen et al., *Science* 239:1534 (1988). However, CDR loop exchanges still do not uniformly result in an antibody with the same binding properties as the antibody of origin. Changes in framework residues (FR), residues involved in CDR loop support, in humanized antibodies also are required to preserve antigen binding affinity. Kabat et al., *J. Immunol.* 147:1709 (1991). While the use of CDR grafting and framework residue preservation in a number of humanized antibody constructs has been reported, it is difficult to predict if a particular sequence will result in the antibody with the desired binding, and sometimes biological, properties. See, e.g., Queen et al., *Proc. Natl. Acad. Sci. USA* 86:10029 (1989), Gorman et al., *Proc. Natl. Acad. Sci. USA* 88:4181 (1991), and Hodgson, *Bio/Technology* 9:421 (1991). Moreover, most prior studies used different human sequences for animal light and heavy variable sequences, rendering the predictive nature of such studies questionable. Sequences of known antibodies have been used or, more typically, those of antibodies having known X-ray structures, antibodies NEW and KOL. See, e.g., Jones et al., supra; Verhoeyen et al., supra; and Gorman et al., supra. Exact sequence information has been reported for only a few humanized constructs.

The present invention provides humanized monoclonal antibodies which recognize human IL-10 and modulate its activity, in particular with regard to autoimmune disorders. The humanized antibody should provide an alternative therapy choice without the toxicity and non-specificity associated with current treatments.

BRIEF SUMMARY OF THE INVENTION

Provided herein is a humanized recombinant antibody molecule that binds IL-10, or binding fragment thereof, comprising: at least one antibody light chain variable region, or binding fragment thereof, comprising a polypeptide having at least one amino acid sequence selected from the group consisting of SEQ ID NO:1 at CDR1, SEQ ID NO:2 at CDR2, and SEQ ID NO:3 at CDR3; and a framework region, wherein the amino acid sequence of framework region is all or substantially all of a human immunoglobin amino acid sequence; and at least one antibody heavy chain variable region, or binding fragment thereof, comprising a polypeptide having at least one amino acid sequence selected from the group of SEQ ID NO:6 at CDR1, SEQ ID NO:7 at CDR2, and SEQ ID NO:8 at CDR3; and a framework region, wherein the amino acid sequence of framework region is all or substantially all of a human immunoglobin amino acid sequence. Also provided herein is an antibody, wherein the antibody light chain, or binding fragment thereof, comprises a polypeptide having a variable region of SEQ ID NO:4. In one specific embodiment, the antibody light chain, or binding fragment thereof, comprises a polypeptide having a variable region and a constant region of SEQ ID NO:5. In one specific embodiment, the antibody heavy chain, or binding fragment thereof, comprises a polypeptide having a variable region of SEQ ID NO:9. In another specific embodiment, the antibody heavy chain, or binding fragment thereof, comprises a polypeptide having a variable region and a constant region of SEQ ID NO:10.

Further provided herein is a chimeric recombinant antibody molecule that binds IL-10 or binding fragment thereof, comprising: at least one antibody light chain variable region, or binding fragment thereof, comprising a polypeptide having at least one amino acid sequence selected from the group consisting of SEQ ID NO:1 at CDR1, SEQ ID NO:2 at CDR2, and SEQ ID NO:3 at CDR3; and at least one antibody heavy chain variable region, or binding fragment thereof, comprising a polypeptide having at least one amino acid sequence selected from the group consisting of SEQ ID NO:6 at CDR1, SEQ ID NO:7 at CDR2, and SEQ ID NO:8 at CDR3.

Also provided herein is a humanized recombinant antibody molecule that binds IL-10, or binding fragment thereof, comprising: at least one antibody light chain, or binding fragment thereof, comprising a polypeptide having an amino acid sequence selected from the group consisting of SEQ ID NO:11 at CDR1, SEQ ID NO:12 at CDR2, and SEQ ID NO:13 at CDR3; and a framework region, wherein the amino acid sequence of framework region is all or substantially all of a human immunoglobin amino acid sequence; and at least one antibody heavy chain, or binding fragment thereof, comprising a polypeptide having an amino acid sequence selected from the group consisting of SEQ ID NO:15 at CDR1, SEQ ID NO:16 at CDR2, and SEQ ID NO:17 at CDR3; and a framework region, wherein the amino acid sequence of framework region is all or substantially all of a human immunoglobin amino acid sequence. In one specific embodiment, the antibody light chain, or binding fragment thereof, comprises a polypeptide having a variable region and a constant region of SEQ ID NO:14. In yet another specific embodiment, the antibody heavy chain, or binding fragment thereof, comprises a polypeptide having a variable region and a constant region of SEQ ID NO:18.

Further provided herein is a chimeric recombinant antibody molecule that binds IL-10, or binding fragment thereof, comprising: at least one antibody light chain, or binding fragment thereof, comprising a polypeptide having at least one amino acid sequence selected from the group consisting of SEQ ID NO:11 at CDR1, SEQ ID NO:12 at CDR2, and SEQ ID NO:13 at CDR3; and at least one antibody heavy chain, or binding fragment thereof, comprising a polypeptide having at least one amino acid sequence selected from the group consisting of SEQ ID NO:15 at CDR1, SEQ ID NO:16 at CDR2, and SEQ ID NO:17 at CDR3.

In one embodiment, the antibodies described supra further comprise a heavy chain constant region, wherein the heavy chain constant region comprises a γ1, γ2, γ3, or γ4 human heavy chain constant region or a variant thereof. In one embodiment, the antibodies described above further comprise a light chain constant region, wherein the light chain constant region comprises a lambda or a kappa human light chain constant region. In some embodiments, the binding fragment of these antibodies is an antibody fragment selected from the group consisting of Fab, Fab', Fab'-SH, Fv, scFv, F(ab')$_2$, and a diabody.

Further provided herein is a method of suppressing an immune response in a human subject comprising administering to a subject in need thereof an antibody specific for IL-10, or a binding fragment thereof, in an amount effective to block the biological activity of IL-10, wherein the antibody is an antibody disclosed herein. The immune response suppressed by this method is a humoral or a cellular response. In one embodiment, the subject treated by this method has systemic lupus erythematosus. In another embodiment, the subject has immune thrombocytopenic purpura (ITC). In yet another embodiment, the subject has lupus nephritis. In a further embodiment, the subject has HIV. In another embodiment, the subject has hepatitis C. In one specific embodiment, the method of suppressing an immune response in a human subject comprising administering to a subject in need thereof (1) an antibody specific for IL-10, or a binding fragment thereof, in an amount effective to block the biological activity of IL-10, wherein the antibody is an antibody disclosed herein, and (2) an immunosuppressive agent.

Provided herein is a composition comprising an antibody, or binding fragment thereof, in combination with a pharmaceutically acceptable carrier or diluent, wherein the antibody is one of the antibodies disclosed supra.

Further provided herein is an isolated nucleic acid encoding the polypeptide of the antibodies disclosed supra. Also provided herein is an expression vector comprising the isolated nucleic acid sequence operably linked to control sequences recognized by a host cell transfected with the vector. Provided herein is a host cell comprising the vector comprising the isolated nucleic acid sequence. Further provided herein is a method of producing a polypeptide, comprising culturing the host cell comprising the vector under conditions wherein the nucleic acid sequence is expressed, thereby producing the polypeptide, and recovering the polypeptide from the host cell.

Provided herein is an isolated nucleic acid sequence encoding an antibody specific for IL-10 comprising a light chain having the nucleic acid sequence of SEQ ID NO:19 and a heavy chain having the nucleic acid sequence of SEQ ID NO:20. In further embodiments, the light chain has an American Type Culture Collection (ATCC) deposit number of PTA-5923 and the heavy chain has an ATCC deposit number of PTA-5922.

Provided herein is an isolated nucleic acid sequence encoding an antibody specific for IL-10 comprising a light chain having the nucleic acid sequence of SEQ ID NO:21 and a heavy chain having the nucleic acid sequence of SEQ ID NO:22. In a further embodiment, the light chain has an ATCC deposit number of PTA-5927 and the heavy chain has an ATCC deposit number of PTA-5926.

Further provided herein is an isolated nucleic acid sequence encoding a binding fragment of the antibody encoded by the above nucleic acid sequences. In one embodiment, the binding fragment is an antibody fragment selected from the group consisting of Fab, Fab', Fab'-SH, Fv, scFv, and F(ab')$_2$.

Provided herein is a method to identify an acceptor germline sequence for a humanized antibody, which method comprises the steps of: a) identifying a non-human antibody that has the desired biological activity; b) determining the amino acid sequence of a non-human antibody $V_H$ and $V_L$ domains; and c) comparing the nonhuman antibody sequence to a group of human germline sequences, wherein the comparison comprises the substeps of: 1) assigning the sequence of non-human $V_H$ and $V_L$ domain sequences residue numbers; 2) delineating the CDR and FR regions in the sequence; 3) assigning a predetermined numerical score at each residue position for which the non-human and human germline sequences are identical; and 4) totaling all of the residue scores to generate a total score for each human germline sequence; and d) identifying the human germline sequence with the highest total residue score as the acceptor germline sequence. In one embodiment, the method further comprises the substeps of: 5) assigning a numerical score of 1 for each residue position for which the non-human and human germline sequences are identical that was not scored in substep (3) to germline sequences with identical total residue scores after substep (4); 6) totaling all of the residue scores to generate a total score for each human germline sequence. In a specific embodiment, the non-human antibody is specific for IL-10 and inhibits the biological activity of IL-10. In a specific embodiment, the numerical scores are assigned to the residues as in Tables 2 and 3 for $V_H$ and $V_L$ regions, respectively.

Further provided herein is an antibody generated by the above method.

BRIEF DESCRIPTION OF THE DRAWINGS

FIG. 1A shows the assignment of residue numbers and numerical scores to the potential acceptor germline sequence relative to the variable light chain of the anti-human IL-10 antibody, 12G8 (germline sequences—SEQ ID NOs: 27-30).

FIG. 1B shows the assignment of residue numbers and numerical scores to the potential acceptor germline sequence relative to the variable heavy chain of the anti-human IL-10 antibody, 12G8 (germline sequences—SEQ ID NOs: 31-35).

FIG. 1C shows the assignment of residue numbers and numerical scores to the potential acceptor germline sequence relative to the variable light chain of the anti-human IL-10 antibody, 11D8 (germline sequences—SEQ ID NOs: 27-30).

FIG. 1D shows the assignment of residue numbers and numerical scores to the potential acceptor germline sequence relative to the variable heavy chain of the anti-human IL-10 antibody, 11D8 (germline sequences—SEQ ID NOs: 31-35).

FIG. 2A is a concentration-time profile for 12G8 antibody administered i.v. as described in Example III.

FIG. 2B is a concentration-time profile for 12G8 administered s.c. as described in Example III.

DETAILED DESCRIPTION OF THE INVENTION

Figure 3A:
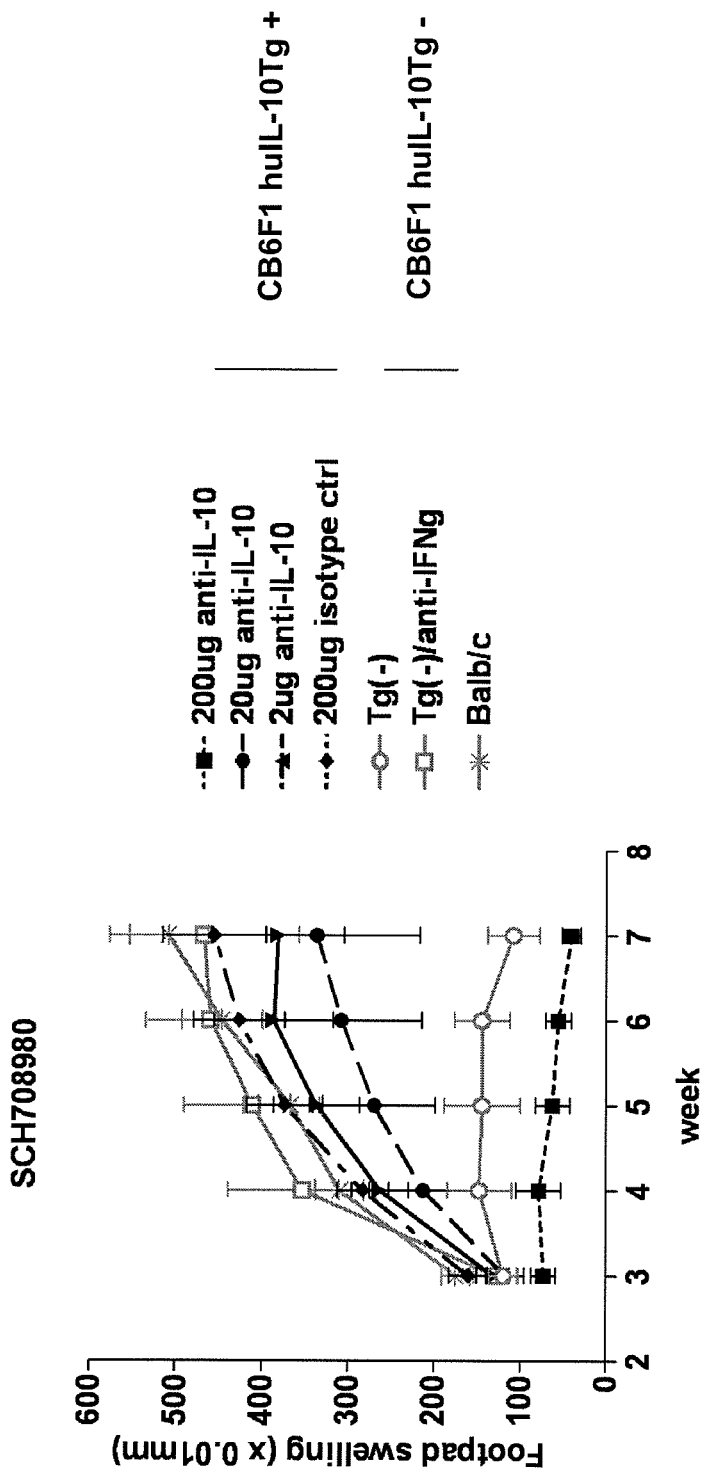
FIG. 3A shows that administration of the humanized anti-IL-10 antibody, SCH708980, confers resistance to Leishmania major infection in IL-10 transgenic mice. Infection was determined by measuring footpad swelling with a caliper at the times indicated. 12G8 antibody was administered as described in Example VI.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, the term "IL-10 binding fragment" or "binding fragment thereof" encompasses a fragment or a derivative of an antibody that still substantially retain its biological activity of inhibiting IL-10 activity. Therefore, the term "antibody fragment" or IL-10 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 50% of its IL-10 inhibitory activity. Preferably, a binding fragment or derivative retains at least 60%, 70%, 80%, 90%, 95%, 99% or 100% of its IL-10 inhibitory activity. It is also intended that a IL-10 binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352: 624-628 (1991) and Marks et al., J. Mol. Biol. 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad Sci. USA 81: 6851-6855 (1984)).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun, THE PHARMACOLOGY OF MONOCLONAL ANTIBODIES, vol. 113, Rosenburg and Moore eds. Springer-Verlag, New York, pp. 269-315 (1994).

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Hollinger et al., Proc. Natl. Acad. Sci. USA 90: 6444-6448 (1993).

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

As used herein, the term "hypervariable region" refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and residues 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol. 196: 901-917 (1987)). As used herein, the term "framework" or "FR" residues refers to those variable domain residues other than the hypervariable region residues defined herein as CDR residues.

As used herein, the term "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., Molecular Biology of the Gene, The Benjamin/Cummings Pub. Co., p. 224 (4th Edition 1987)). Such exemplary substitutions are preferably made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., PCR TECHNOLOGY (Stockton Press, N.Y., 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin may be used.

As used herein, the term "immunosuppressive agent" refers to natural or synthetic agents that suppress or modulate an immune response. The immune response can be a humoral or cellular response.

B. IL-10 SPECIFIC ANTIBODIES

The compositions and methods disclosed herein relate to the modulation of IL-10 activity, particularly in immune responses. Specifically, the compositions and methods herein employ antibodies specific for the cytokine, IL-10. IL-10 is a potent cytokine that modulates T and B cell responses through the regulation of growth, differentiation, and cytokine synthesis of a variety of cell types involved in immune responses. Notably, IL-10 production is frequently associated with autoimmune diseases and pathogen-induced immunopathology. Therefore, a composition, and methods thereof, that modulates and inhibits IL-10 activity can alter the development and sustainment of autoimmune disease and related symptoms and ameliorate or reduce pathogen-associated immunopathology.

Targeting IL-10 activity with humanized antibodies offers several unique advantages. First, targeting IL-10 with antibody permits a specific suppression of IL-10 activity while leaving the remainder of the immune response intact. In many cases of pathogen-induced immunopathology, the reduction or elimination of IL-10 activity should permit the desired effector immune response to eliminate with pathogen without further pathology. For the autoimmune patient, the reduction or elimination of IL-10 activity should reduce or eliminate the disease and/or its symptoms while maintaining the patient's immune competence. Second, humanized IL-10 antibodies circumvents the limitation associated with immunogenic rodent antibodies. The use of human sequences eliminates the immunogenicity of the exogenously administered antibodies, allowing therapeutic administration.

Humanized antibodies contain sequences from non-human as well as human antibodies. Typically, the process of humanization begins with the generation of a non-human antibody that has the desired biological activity, i.e., inhibits IL-10 activity. Once a non-human antibody with the appropriate characteristics is identified, recombinant means are then employed to create a hybrid sequence using non-human and human sequences.

C. GENERATION of IL-10 SPECIFIC ANTIBODIES

Any suitable method for generating monoclonal antibodies may be used. For example, a recipient may be immunized with IL-10 or a fragment thereof. Any suitable method of immunization can be used. Such methods can include adjuvants, other immunostimulants, repeated booster immunizations, and the use of one or more immunization routes.

Any suitable source of IL-10 can be used as the immunogen for the generation of the non-human antibody of the compositions and methods disclosed herein. Such forms include, but are not limited whole protein, peptide(s), and epitopes, generated through recombinant, synthetic, chemical or enzymatic degradation means known in the art. IL-10 is an acid-sensitive, noncovalent homodimer of two interpenetrating polypeptide chain. The cytokine is 160 amino acids in length with well conserved sequences that include an α-helical bundle structure similar to interferons and hemopoietic cytokines Human and murine IL-10 have 73% amino acid homology, with human IL-10 being active on murine and human cells. IL-10 is commercially available or can be produced using well known molecular biology techniques. Genbank cDNA sequences are available for the human, pig-tailed macaque, mangabey, rhesus, and owl monkeys, lemur, mouse, rat, guinea pig, Syrian hamster, rabbit, cat, dog, as well as others. Recombinant human IL-10 is a 17-18 kDa polypeptide that is not N-glycosylated.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit IL-10. It is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle, et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275-1281.

Other suitable techniques involve selection of libraries of antibodies in phage or similar vectors. See, e.g., Huse et al., *Science* 246:1275-1281 (1989); and Ward et al., *Nature* 341: 544-546 (1989). The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci. USA* 86:10029-10033; or made in transgenic mice, see Mendez et al. (1997) *Nature Genetics* 15:146-156; also see Abgenix and Medarex technologies.

Antibodies or binding compositions against predetermined fragments of IL-10 can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective IL-10. These monoclonal antibodies will usually bind with at least a $K_d$ of about 1 µM, more usually at least about 300 nM, typically at least about 30 nM, preferably at least about 10 nM, more preferably at least about 3 nM or better, usually determined by ELISA. Suitable non-human antibodies may also be identified using the biologic assays described in Section D infra.

C. HUMANIZATION of IL-10 SPECIFIC ANTIBODIES

Any suitable non-human antibody can be used as a source for the hypervariable region. Sources for non-human antibodies include, but are not limited to, murine, lupine, bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance of the desired biological activity. For further details, see Jones et al., *Nature* 321: 522-525 (1986); Reichmann et al., *Nature* 332: 323-329 (1988); and Presta, *Curr. Op. Struct. Biol.* 2: 593-596 (1992).

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239 400).

Amino acid sequence variants of humanized anti-IL-10 antibody are prepared by introducing appropriate nucleotide changes into the humanized anti-IL-10 antibody DNA, or by peptide synthesis. Such variants include, for example, deletions from, and/or insertions into and/or substitutions of, residues within the amino acid sequences shown for the humanized anti-IL-10 F(ab) (e.g. as in SEQ ID NO's 5 and 10). Any combination of deletion, insertion, and substitution is made to arrive at the final construct, provided that the final construct possesses the desired characteristics. The amino acid changes also may alter post-translational processes of the humanized anti-IL-10 antibody, such as changing the number or position of glycosylation sites.

A useful method for identification of certain residues or regions of the humanized anti-IL-10 antibody polypeptide that are preferred locations for mutagenesis is called "alanine scanning mutagenesis," as described by Cunningham and Wells, *Science* 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with IL-10 antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed humanized anti-IL-10 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-IL-10 antibody with an N-terminal methionyl residue or the antibody fused to an epitope tag. Other insertional variants of the humanized anti-IL-10 antibody molecule include the fusion to the N- or C-terminus of humanized anti-IL-10 antibody of an enzyme or a polypeptide which increases the serum half-life of the antibody.

Another type of variant is an amino acid substitution variant. These variants have at least one amino acid residue in the humanized anti-IL-10 antibody molecule removed and a different residue inserted in its place. The sites of greatest interest for substitutional mutagenesis include the hypervariable loops, but FR alterations are also contemplated. Tables 2 and 3 in the method described below provides guidance as to hypervariable region residues which can be altered. Hypervariable region residues or FR residues involved in antigen binding are generally substituted in a relatively conservative manner.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of humanized IL-10 specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IL-10 antibody.

Ordinarily, amino acid sequence variants of the humanized anti-IL-10 antibody will have an amino acid sequence having at least 75% amino acid sequence identity with the original humanized antibody amino acid sequences of either the heavy or the light chain (e.g. as in SEQ ID NO:5 and 10), more preferably at least 80%, more preferably at least 85%, more preferably at least 90%, and most preferably at least 95%. Identity or homology with respect to this sequence is defined herein as the percentage of amino acid residues in the candidate sequence that are identical with the humanized anti-IL-10 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is a IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

CDR and FR residues are determined according to the standard sequence definition of Kabat. Kabat et al., Sequences of Proteins of Immunological Interest, National Institutes of Health, Bethesda Md. (1987).

Provided herein is a method to identify an acceptor germline sequence for a humanized antibody, which method comprises the steps of: a) identifying a non-human antibody that has the desired biological activity; b) determining the amino acid sequence of a non-human antibody $V_H$ and $V_L$ domains; and c) comparing the nonhuman antibody sequence to a group of human germline sequences, wherein the comparison comprises the substeps of: 1) assigning the non-human V sequences residue numbers according to Kabat supra; 2) delineating the CDR and FR regions in the sequence according to Kabat supra; 3) assigning a predetermined numerical score at specific residue position for which the non-human and human antibody germline sequences are identical; and 4) totaling all of the residue scores to generate a total score for each human germline sequence; and d) identifying the human germline sequence with the highest total residue score as the acceptor germline sequence. In one embodiment, the method further comprises the substeps of: 5) assigning a numerical score of 1 for each FR residue position for which the non-human and human antibody germline sequences are identical that was not scored in substep (3) to germline sequences with identical total residue scores after substep (4); 6) totaling all of the residue scores to generate a total score for each human germline sequence. In a specific embodiment, the non-human antibody is specific for IL-10 and inhibits the biological activity of IL-10. Also provided herein is an antibody generated by the above method.

In one embodiment, the IL-10 antibody is humanized using the following method. First, the non-human $V_L$ and $V_H$ domains of the IL-10 antibody are cloned and sequenced, and the amino acid sequence determined. Then, the non-human $V_H$ sequence are compared to a group of five human $V_H$ germline amino acid sequences. The five groups contain one representative from the subgroups IGHV1 and IGHV4 and three representatives from subgroup IGHV3. The $V_H$ subgroups are listed in M.-P. Lefranc, Exp. Clin. Immunogenetics, 18:100-116 (2001). Specifically, the comparison with the five germline sequences begins with the assignment of residue numbers to the non-human $V_H$ sequence according to the Kabat numbering system. See Kabat, et al., U.S. Department of Health and Human Services, NIH Pub. 91-3242 (5th Ed., 1991). The non-human $V_H$ sequence are then aligned with each of the five human germline sequences. Since the V genes only comprise $V_H$ residues 1-94, only these residues are considered in the alignment. Next, the complementarity-determining (CDR) and framework (FR) regions in the sequence are delineated. CDR and FR are delineated according to the combination of the definitions provided in Kabat, et al., U.S. Department of Health and Human Services, NIH Pub. 91-3242 (5th Ed., 1991), and C. Chothia & A. M. Lesk, J. Mol. Biol., 196:901-917 (1987). Therefore, the CDR definition used is residues 26-35 for CDR1, residues 50-65 for CDR2, and CDR3 is residues 95-102 for CDR3 of the $V_H$ domain. The next step involves assigning a numerical score at identified residue position where the non-human and human sequences are identical. One example of this scoring is shown in Table 2 below.

TABLE 2

| Residue # | Score | Reason |
| --- | --- | --- |
| 2 | 4 | Affects CDR-H1,3* |
| 4 | 3 | Affects CDR-H1,3 |
| 24 | 3 | Affects CDR-H1 |
| 26 | 4 | Affects CDR-H1* |
| 27 | 4 | Affects CDR-H1,3* |
| 29 | 4 | Affects CDR-H1* |
| 34 | 4 | Affects CDR-H1* |
| 35 | 2 | VH/VL interface |
| 37 | 2 | VH/VL interface |
| 39 | 2 | VH/VL interface |
| 44 | 2 | VH/VL interface |
| 45 | 2 | VH/VL interface |
| 47 | 4 | VH/VL interface, CDR-L3 |
| 48 | 3 | Affects CDR-H2 |
| 49 | 3 | Affects CDR-H2 |
| 50 | 2 | VH/VL interface |
| 51 | 3 | Affects CDR-H2 |
| 58 | 2 | VH/VL interface |
| 59 | 3 | Affects CDR-H2 |
| 60 | 2 | VH/VL interface |
| 63 | 3 | Affects CDR-H2 |
| 67 | 3 | Affects CDR-H2 |
| 69 | 3 | Affects CDR-H2 |
| 71 | 4 | Affects CDR-H2* |
| 73 | 3 | Affects CDR-H1 |
| 76 | 3 | Affects CDR-H1 |
| 78 | 3 | Affects CDR-H1 |
| 91 | 2 | VH/VL interface |
| 93 | 3 | Affects CDR-H3 |
| 94 | 4 | Affects CDR-H3* | max 89
*Noted as affecting CDR conformation in C. Chothia et al, Nature 342: 877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following residues: 1, 3, 5-23, 25, 36, 38, 40-43, 46, 66, 68, 70, 72, 74, 75, 77, 79-90, and 92 (max 49). The residue scores are totaled again, and the acceptor germline sequence is the one with the highest total score. If two or more germline sequences still have identical scores, either one can be used as the acceptor germline sequence.

If the $V_L$ sequence is a member of the kappa subclass of $V_L$, the non-human $V_L$ sequence from the IL-10 specific antibody is compared to a group of four human $V_L$ kappa germline amino acid sequences. The four sequences are comprised of one representative from each of four established human $V_L$ subgroups listed in V. Barbie & M.-P. Lefranc, Exp. Clin. Immunogenetics 15:171-183 (1998) and M.-P. Lefranc, Exp. Clin. Immunogenetics 18:161-174 (2001). The four sequences also correspond to the four subgroups listed in Kabat et al., U.S. Department of Health and Human Services, NIH Pub. 91-3242, pp. 103-130 (5th Ed., 1991). The comparison of the non-human sequence to the four germline sequences begins with the assignment of residue numbers to the non-human $V_L$ sequence residues according to Kabat et al., U.S. Department of Health and Human Services, NIH Pub. 91-3242 (5th Ed., 1991). The non-human $V_L$ sequences are then aligned with each of the four human germline sequences. Since the V genes only comprise $V_L$ residues 1-95, only these residues are considered in the alignment. Next, the complementarity-determining (CDR) and framework (FR) regions are delineated in the sequence. CDR and FR are delineated according to the combination of the definitions provided in Kabat et al., U.S. Department of Health and Human Services, NIH Pub. 91-3242 (5th Ed. 1991), and C. Chothia & A. M. Lesk, J. Mol. Biol., 196:901-917 (1987). Therefore, the CDR definition used is residues 24-34 for CDR1, residues 50-56 for CDR2, and residues 89-97 for CDR3 of the $V_L$ domain. The next step involves assigning a numerical score at identified residue position where the non-human and human sequences are identical. One example of this scoring is shown in Table 3 below.

TABLE 3

| Residue # | Score | Reason |
| --- | --- | --- |
| 2 | 4 | Affects CDR-L1,3* |
| 4 | 3 | Affects CDR-L1,3 |
| 25 | 4 | Affects CDR-L1* |
| 29 | 4 | Affects CDR-L1,3* |
| 33 | 4 | Affects CDR-L1,3* |
| 34 | 2 | VL/VH interface |
| 36 | 2 | VL/VH interface |
| 38 | 2 | VL/VH interface |
| 43 | 2 | VL/VH interface |
| 44 | 2 | VL/VH interface |
| 46 | 4 | VL/VH interface, CDR-H3 |
| 47 | 3 | Affects CDR-L2 |
| 48 | 4 | Affects CDR-L2* |
| 49 | 2 | VL/VH interface |
| 55 | 2 | VL/VH interface |
| 58 | 3 | Affects CDR-L2 |
| 62 | 3 | Affects CDR-L2 |
| 64 | 4 | Affects CDR-L2* |
| 71 | 4 | Affects CDR-L1* |
| 87 | 2 | VL/VH interface |
| 89 | 2 | VL/VH interface |
| 90 | 4 | Affects CDR-L3* |
| 91 | 2 | VL/VH interface |

TABLE 3-continued

| Residue # | Score | Reason |
|---|---|---|
| 94 | 2 | VL/VH interface |
| 95 | 4 | Affects CDR-L3* |

*Noted as affecting CDR conformation in C. Chothia et al, *Nature* 342: 877-883, (1989).

After the residue positions are assigned a numerical score, all of the residue scores are totaled. The acceptor germline sequence is the one with the highest total score. In a case where two or more germline sequences have identical scores, then add 1 to the total for each position where the non-human and human sequences are IDENTICAL for the following residues: 1, 3, 5-23, 35, 37, 39-42, 57, 59-61, 63, 65-70, 72-86, and 88. The residue scores are totaled again, and the acceptor germline sequence is the one with the highest total score. If two or more germline sequences still have identical scores, either one can be used as the acceptor germline sequence.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

In one embodiment, the antibody is a humanized recombinant antibody molecule that binds IL-10, or binding fragment thereof, comprising: at least one antibody light chain variable region, or binding fragment thereof, comprising a polypeptide having at least one amino acid sequence selected from the group consisting of SEQ ID NO:1 (KTSQNIFENLA) at CDR1, SEQ ID NO:2 (NASPLQA) at CDR2, and SEQ ID NO:3 (HQYYSGYT) at CDR3; and a framework region, wherein the amino acid sequence of framework region is all or substantially all of a human immunoglobin amino acid sequence; and at least one antibody heavy chain variable region, or binding fragment thereof, comprising a polypeptide having at least one amino acid sequence selected from the group consisting of SEQ ID NO:6 (GFTFSDYHMA) at CDR1, SEQ ID NO:7 (SITLDATYTYYRDSVRG) at CDR2, SEQ ID NO:8 (HRGFSVWLDY) at CDR3; and a framework region, wherein the amino acid sequence of framework region is all or substantially all of a human immunoglobin amino acid sequence. In a specific embodiment, the antibody light chain, or binding fragment thereof, comprises a polypeptide having a variable region of SEQ ID NO:4 (DIQMTQSPSSL-SASVGDRVTITCKTSQNIFENLAWYQQK-PGKAPKLLIY NASPLQAGVPSRFSGSGSGTDFTLTISS-LQPEDFATYYCHQYYSG-YTFGPGTKLELKRT). In one specific embodiment, the antibody light chain, or binding fragment thereof, comprises a polypeptide having a variable region and a constant region of SEQ ID NO:5. See Table 4. In one specific embodiment, the antibody heavy chain, or binding fragment thereof, comprises a polypeptide having a variable region of SEQ ID NO:9 (QVQLVESGGGVVQPGRSL-RLSCAASGFTFSDYHMAWV RQAPGKGLEWVASITLDATYTYYRDSVR-GRFTISRDNSKNTLYLQMNSLRAEDTAVYY CAR-HRGFSVWLDYWGQGTLVTVSS). In another specific embodiment, the antibody heavy chain, or binding fragment thereof, comprises a polypeptide having a variable region and a constant region of SEQ ID NO:10. See Table 5.

Plasmids containing the nucleic acids encoding the humanized 12G8 light and heavy chains were deposited with the American Type Culture Collection (ATCC) as deposit numbers PTA-5923 and PTA-5922, respectively.

TABLE 4

Full length sequences for light chain of the humanized 12G8 antibody

SEQ ID NO: 5 Full length amino acid sequence of humanized 12G8 antibody
SEQ ID NO: 19 Full length nucleic acid sequence of humanized 12G8 antibody

```
--> variable light domain
 D   I   Q   M   T   Q   S   P   S   S   L   S   A   S   V   G   D   R   V   T   I   T
GAC ATC CAG ATG ACC CAG TCT CCA TCC TCC CTG TCT GCA TCT GTA GGA GAC AGA GTC ACC ATC ACT C   K   T   S   Q   N   I   F   E   N   L   A   W   Y   Q   Q   K   P   G   K   A   P
TGC AAG ACA AGT CAG AAC ATT TTT GAG AAC TTG GCC TGG TAT CAG CAG AAA CCA GGG AAA GCC CCT K   L   L   I   Y   N   A   S   P   L   Q   A   G   V   P   S   R   F   S   G   S   G
AAG CTC CTG ATC TAT AAT GCA AGC CCT TTG CAA GCG GGG GTC CCA TCA AGG TTC AGT GGC AGT GGA S   G   T   D   F   T   L   T   I   S   S   L   Q   P   E   D   F   A   T   Y   Y   C
TCT GGG ACA GAT TTC ACT CTC ACC ATC AGC AGT CTG CAA CCT GAA GAT TTT GCA ACT TAC TAC TGT --> human
 H   Q   Y   Y   S   G   Y   T   F   G   P   G   T   K   L   E   L   K   R   T   V   A
CAC CAG TAT TAT AGC GGG TAC ACG TTT GGA CCT GGG ACC AAG CTG GAA CTG AAA CGT ACG GTG GCT light constant domain
 A   P   S   V   F   I   F   P   P   S   D   E   Q   L   K   S   G   T   A   S   V   V
GCA CCA TCT GTC TTC ATC TTC CCG CCA TCT GAT GAG CAG TTG AAA TCT GGA ACT GCC TCT GTT GTG C   L   L   N   N   F   Y   P   R   E   A   K   V   Q   W   K   V   D   N   A   L   Q
TGC CTG CTG AAT AAC TTC TAT CCC AGA GAG GCC AAA GTA CAG TGG AAG GTG GAT AAC GCC CTC CAA S   G   N   S   Q   E   S   V   T   E   Q   D   S   K   D   S   T   Y   S   L   S   S
TCG GGT AAC TCC CAG GAG AGT GTC ACA GAG CAG GAC AGC AAG GAC AGC ACC TAC AGC CTC AGC AGC
```

TABLE 4-continued

Full length sequences for light chain of the humanized 12G8 antibody

```
 T   L   T   L   S   K   A   D   Y   E   K   H   K   V   Y   A   C   E   V   T   H   Q
ACC CTG ACG CTG AGC AAA GCA GAC TAC GAG AAA CAC AAA GTC TAC GCC TGC GAA GTC ACC CAT CAG

G   L   S   S   P   V   T   K   S   F   N   R   G   E   C
GGC CTG AGC TCG CCC GTC ACA AAG AGC TTC AAC AGG GGA GAG TGT
```

TABLE 5

Full length sequences for heavy chain of the humanized 12G8 antibody

SEQ ID NO: 10 Full length amino acid sequence of humanized 12G8 antibody
SEQ ID NO: 20 Full length nucleic acid sequence of humanized 12G8 antibody

```
 Q   V   Q   L   V   E   S   G   G   G   V   V   Q   P   G   R   S   L   R   L   S   C
CAG GTG CAG CTG GTG GAG TCT GGG GGA GGC GTG GTC CAG CCT GGG AGG TCC CTG AGA CTC TCC TGT

A   A   S   G   F   T   F   S   D   Y   H   M   A   W   V   R   Q   A   P   G   K   G
GCA GCC TCT GGA TTC ACT TTC AGT GAC TAT CAT ATG GCC TGG GTC CGC CAG GCT CCA GGC AAG GGG

L   E   W   V   A   S   I   T   L   D   A   T   Y   T   Y   Y   R   D   S   V   R   G
CTG GAG TGG GTG GCA AGC ATT ACT CTT GAT GCT ACC TAC ACT TAC TAT CGC GAC TCC GTG CGC GGC

R   F   T   I   S   R   D   N   S   K   N   T   L   Y   L   Q   M   N   S   L   R   A
CGC TTC ACC ATC TCC AGA GAC AAT TCC AAG AAC ACG CTG TAT CTG CAA ATG AAC AGC CTG AGA GCT

E   D   T   A   V   Y   Y   C   A   R   H   G   F   S   V   W   L   D   Y   W   G
GAG GAC ACG GCT GTG TAT TAC TGT GCG AGA CAT CGA GGC TTT AGC GTC TGG CTT GAT TAC TGG GGC
                                            --> human IgG1 constant heavy domains
 Q   G   T   L   V   T   V   S   S   A   S   T   K   G   P   S   V   F   P   L   A   P
CAA GGC ACC CTG GTC ACC GTC TCG TCG GCT AGC ACC AAG GGC CCA TCG GTC TTC CCC CTG GCA CCC S   S   K   S   T   S   G   G   T   A   A   L   G   C   L   V   K   D   Y   F   P   E
TCC TCC AAG AGC ACC TCT GGG GGC ACA GCG GCC CTG GGC TGC CTG GTC AAG GAC TAC TTC CCC GAA P   V   T   V   S   W   N   S   G   A   L   T   S   G   V   H   T   F   P   A   V   L
CCG GTG ACG GTG TCG TGG AAC TCA GGC GCC CTG ACC AGC GGC GTG CAC ACC TTC CCG GCT GTC CTA Q   S   S   G   L   Y   S   L   S   S   V   V   T   V   P   S   S   S   L   G   T   Q
CAG TCC TCA GGA CTC TAC TCC CTC AGC AGC GTG GTG ACC GTG CCC TCC AGC AGC TTG GGC ACC CAG T   Y   I   C   N   V   N   H   K   P   S   N   T   K   V   D   K   K   V   E   P   K
ACC TAC ATC TGC AAC GTG AAT CAC AAG CCC AGC AAC ACC AAG GTG GAC AAG AAA GTT GAG CCC AAA S   C   D   K   T   H   T   C   P   P   C   P   A   P   E   L   L   G   G   P   S   V
TCT TGT GAC AAA ACT CAC ACA TGC CCA CCG TGC CCA GCA CCT GAA CTC CTG GGG GGA CCG TCA GTC F   L   F   P   P   K   P   K   D   T   L   M   I   S   R   T   P   E   V   T   C   V
TTC CTC TTC CCC CCA AAA CCC AAG GAC ACC CTC ATG ATC TCC CGG ACC CCT GAG GTC ACA TGC GTG V   V   D   V   S   H   E   D   P   E   V   K   F   N   W   Y   V   D   G   V   E   V
GTG GTG GAC GTG AGC CAC GAA GAC CCT GAG GTC AAG TTC AAC TGG TAC GTG GAC GGC GTG GAG GTG H   N   A   K   T   K   P   R   E   E   Q   Y   N   S   T   Y   R   V   V   S   V   L
CAT AAT GCC AAG ACA AAG CCG CGG GAG GAG CAG TAC AAC AGC ACG TAC CGT GTG GTC AGC GTC CTC T   V   L   H   Q   D   W   L   N   G   K   E   Y   K   C   K   V   S   N   K   A   L
ACC GTC CTG CAC CAG GAC TGG CTG AAT GGC AAG GAG TAC AAG TGC AAG GTC TCC AAC AAA GCC CTC P   A   P   I   E   K   T   I   S   K   A   K   G   Q   P   R   E   P   Q   V   Y   T
CCA GCC CCC ATC GAG AAA ACC ATC TCC AAA GCC AAA GGG CAG CCC CGA GAA CCA CAG GTG TAC ACC L   P   P   S   R   D   E   L   T   K   N   Q   V   S   L   T   C   L   V   K   G   F
CTG CCC CCA TCC CGG GAT GAG CTG ACC AAG AAC CAG GTC AGC CTG ACC TGC CTG GTC AAA GGC TTC Y   P   S   D   I   A   V   E   W   E   S   N   G   Q   P   E   N   N   Y   K   T   T
TAT CCC AGC GAC ATC GCC GTG GAG TGG GAG AGC AAT GGG CAG CCG GAG AAC AAC TAC AAG ACC ACG P   P   V   L   D   S   D   G   S   F   F   L   Y   S   K   L   T   V   D   K   S   R
CCT CCC GTG CTG GAC TCC GAC GGC TCC TTC TTC CTC TAC AGC AAG CTC ACC GTG GAC AAG AGC AGG
```

TABLE 5-continued

Full length sequences for heavy chain of the humanized 12G8 antibody

| W | Q | Q | G | N | V | F | S | C | S | V | M | H | E | A | L | H | N | H | Y | T | Q |
|---|---|---|---|---|---|---|---|---|---|---|---|---|---|---|---|---|---|---|---|---|---|
| TGG | CAG | CAG | GGG | AAC | GTC | TTC | TCA | TGC | TCC | GTG | ATG | CAT | GAG | GCT | CTG | CAC | AAC | CAC | TAC | ACG | CAG |

| K | S | L | S | L | S | P | G | K |
|---|---|---|---|---|---|---|---|---|
| AAG | AGC | CTC | TCC | CTG | TCT | CCG | GGT | AAA |

In one embodiment, the antibody is a humanized recombinant antibody molecule that binds IL-10, or binding fragment thereof, comprising: at least one antibody light chain, or binding fragment thereof, comprising a polypeptide having at least one amino acid sequence selected from the group consisting of SEQ ID NO:11 (RASESVDDYGHSFMH) at CDR1, SEQ ID NO:12 (RASTLES) at CDR2, and SEQ ID NO:13 (QQGNEDPWT) at CDR3; and a framework region, wherein the amino acid sequence of framework region is all or substantially all of a human immunoglobin amino acid sequence; and at least one antibody heavy chain, or binding fragment thereof, comprising a polypeptide having at least one amino acid sequence selected from the group consisting of SEQ ID NO:15 (GFSLTNYGVH) at CDR1, SEQ ID NO:16 (VIWSGGSTDYNAAFIS) at CDR2, and SEQ ID NO:17 (NRGYDVYFDY) at CDR3; and a framework region, wherein the amino acid sequence of framework region is all or substantially all of a human immunoglobin amino acid sequence. In one specific embodiment, the antibody light chain, or binding fragment thereof, comprises a polypeptide having a variable region and a constant region of SEQ ID NO:14. See Table 6. In yet another specific embodiment, the antibody heavy chain, or binding fragment thereof, comprises a polypeptide having a variable region and a constant region of SEQ ID NO:18. See Table 7.

Plasmids containing the humanized 11D8 heavy and light chains were deposited with the ATCC as deposit numbers PTA-5926 and PTA-5927, respectively.

TABLE 6

Full length sequences for light chain of the humanized 11D8 antibody

SEQ ID NO: 14 Full length amino acid sequence for humanized 11D8 antibody
SEQ ID NO: 21 Full length nucleotide sequence for humanized 11D8 antibody

| E | I | V | L | T | Q | S | P | G | T | L | S | L | S | P | G | E | R | A | T |
|---|---|---|---|---|---|---|---|---|---|---|---|---|---|---|---|---|---|---|---|
| GAA | ATT | GTG | TTG | ACG | CAG | TCT | CCA | GGC | ACC | CTG | TCT | TTG | TCT | CCA | GGG | GAA | AGA | GCC | ACC |

| L | S | C | R | A | S | E | S | V | D | D | Y | G | H | S | F | M | H | W | Y |
|---|---|---|---|---|---|---|---|---|---|---|---|---|---|---|---|---|---|---|---|
| CTC | TCC | TGC | AGA | GCC | AGT | GAA | AGT | GTT | GAT | GAT | TAT | GGC | CAT | AGT | TTT | ATG | CAC | TGG | TAC |

| Q | Q | K | P | G | Q | A | P | R | L | L | I | Y | R | A | S | T | L | E | S |
|---|---|---|---|---|---|---|---|---|---|---|---|---|---|---|---|---|---|---|---|
| CAG | CAG | AAA | CCT | GGC | CAG | GCT | CCC | AGG | CTC | CTC | ATC | TAT | CGT | GCA | TCC | ACC | CTA | GAA | TCT |

| G | I | P | D | R | F | S | G | S | G | S | G | T | D | F | T | L | T | I | S |
|---|---|---|---|---|---|---|---|---|---|---|---|---|---|---|---|---|---|---|---|
| GGC | ATC | CCA | GAC | AGG | TTC | AGT | GGC | AGT | GGG | TCT | GGG | ACA | GAC | TTC | ACT | CTC | ACC | ATC | AGC |

| R | L | E | P | E | D | F | A | V | Y | Y | C | Q | Q | G | N | E | D | P | W |
|---|---|---|---|---|---|---|---|---|---|---|---|---|---|---|---|---|---|---|---|
| AGA | CTG | GAG | CCT | GAA | GAT | TTT | GCA | GTG | TAT | TAC | TGT | CAG | CAA | GGT | AAT | GAG | GAT | CCG | TGG |

| T | F | G | Q | G | T | K | V | E | I | K | R | T | V | A | A | P | S | V | F |
|---|---|---|---|---|---|---|---|---|---|---|---|---|---|---|---|---|---|---|---|
| ACG | TTC | GGT | CAA | GGT | ACC | AAG | GTG | GAA | ATC | AAG | CGT | ACG | GTG | GCT | GCA | CCA | TCT | GTC | TTC |

| I | F | P | P | S | D | E | Q | L | K | S | G | T | A | S | V | V | C | L | L |
|---|---|---|---|---|---|---|---|---|---|---|---|---|---|---|---|---|---|---|---|
| ATC | TTC | CCG | CCA | TCT | GAT | GAG | CAG | TTG | AAA | TCT | GGA | ACT | GCC | TCT | GTT | GTG | TGC | CTG | CTG |

| N | N | F | Y | P | R | E | A | K | V | Q | W | K | V | D | N | A | L | Q | S |
|---|---|---|---|---|---|---|---|---|---|---|---|---|---|---|---|---|---|---|---|
| AAT | AAC | TTC | TAT | CCC | AGA | GAG | GCC | AAA | GTA | CAG | TGG | AAG | GTG | GAT | AAC | GCC | CTC | CAA | TCG |

| G | N | S | Q | E | S | V | T | E | Q | D | S | K | D | S | T | Y | S | L | S |
|---|---|---|---|---|---|---|---|---|---|---|---|---|---|---|---|---|---|---|---|
| GGT | AAC | TCC | CAG | GAG | AGT | GTC | ACA | GAG | CAG | GAC | AGC | AAG | GAC | AGC | ACC | TAC | AGC | CTC | AGC |

| S | T | L | T | L | S | K | A | D | Y | E | K | H | K | V | Y | A | C | E | V |
|---|---|---|---|---|---|---|---|---|---|---|---|---|---|---|---|---|---|---|---|
| AGC | ACC | CTG | ACG | CTG | AGC | AAA | GCA | GAC | TAC | GAG | AAA | CAC | AAA | GTC | TAC | GCC | TGC | GAA | GTC |

| T | H | Q | G | L | S | S | P | V | T | K | S | F | N | R | G | E | C |
|---|---|---|---|---|---|---|---|---|---|---|---|---|---|---|---|---|---|
| ACC | CAT | CAG | GGC | CTG | AGC | TCG | CCC | GTC | ACA | AAG | AGC | TTC | AAC | AGG | GGA | GAG | TGT |

TABLE 7

Full length sequences for heavy chain of the humanized 11D8 antibody

SEQ ID NO: 18 Full length amino acid sequence for humanized 11D8 antibody
SEQ ID NO: 22 Full length nucleotide sequence for humanized 11D8 antibody

```
Q   V   Q   L   V   E   S   G   G   G   V   V   Q   P   G   R   S
CAG GTG CAG CTG GTG GAG TCT GGG GGA GGC GTG GTC CAG CCT GGG AGG TCC

L   R   L   S   C   A   A   S   G   F   S   L   T   N   Y   G   V   H   W   V
CTG AGA CTC TCC TGT GCA GCC TCT GGT TTC TCA TTA ACA AAC TAT GGT GTA CAC TGG GTC

R   Q   A   P   G   K   G   L   E   W   V   A   V   I   W   S   G   G   S   T
CGC CAG GCT CCA GGC AAG GGG CTG GAG TGG GTG GCA GTG ATA TGG AGT GGT GGA AGC ACA

D   Y   N   A   A   F   I   S   R   F   T   I   S   R   D   N   S   K   N   T
GAC TAT AAT GCA GCT TTC ATA TCC CGA TTC ACC ATC TCC AGA GAC AAT TCC AAG AAC ACG

L   Y   L   Q   M   N   S   L   R   A   E   D   T   A   V   Y   Y   C   A   R
CTG TAT CTG CAA ATG AAC AGC CTG AGA GCT GAG GAC ACG GCT GTG TAT TAC TGT GCG AGA

N   R   G   Y   D   V   Y   F   D   Y   W   G   Q   G   T   L   V   T   V   S
AAT AGG GGG TAC GAC GTC TAC TTT GAC TAC TGG GGC CAA GGC ACC CTT GTC ACA GTC TCG

S   A   S   T   K   G   P   S   V   F   P   L   A   P   S   S   K   S   T   S
TCG GCT AGC ACC AAG GGC CCA TCG GTC TTC CCC CTG GCA CCC TCC TCC AAG AGC ACC TCT

G   G   T   A   A   L   G   C   L   V   K   D   Y   F   P   E   P   V   T   V
GGG GGC ACA GCG GCC CTG GGC TGC CTG GTC AAG GAC TAC TTC CCC GAA CCG GTG ACG GTG

S   W   N   S   G   A   L   T   S   G   V   H   T   F   P   A   V   L   Q   S
TCG TGG AAC TCA GGC GCC CTG ACC AGC GGC GTG CAC ACC TTC CCG GCT GTC CTA CAG TCC

S   G   L   Y   S   L   S   S   V   V   T   V   P   S   S   S   L   G   T   Q
TCA GGA CTC TAC TCC CTC AGC AGC GTG GTG ACC GTG CCC TCC AGC AGC TTG GGC ACC CAG

T   Y   I   C   N   V   N   H   K   P   S   N   T   K   V   D   K   K   V   E
ACC TAC ATC TGC AAC GTG AAT CAC AAG CCC AGC AAC ACC AAG GTG GAC AAG AAA GTT GAG

P   K   S   C   D   K   T   H   T   C   P   P   C   P   A   P   E   L   L   G
CCC AAA TCT TGT GAC AAA ACT CAC ACA TGC CCA CCG TGC CCA GCA CCT GAA CTC CTG GGG

G   P   S   V   F   L   F   P   P   K   P   K   D   T   L   M   I   S   R   T
GGA CCG TCA GTC TTC CTC TTC CCC CCA AAA CCC AAG GAC ACC CTC ATG ATC TCC CGG ACC

P   E   V   T   C   V   V   V   D   V   S   H   E   D   P   E   V   K   F   N
CCT GAG GTC ACA TGC GTG GTG GTG GAC GTG AGC CAC GAA GAC CCT GAG GTC AAG TTC AAC

W   Y   V   D   G   V   E   V   H   N   A   K   T   K   P   R   E   E   Q   Y
TGG TAC GTG GAC GGC GTG GAG GTG CAT AAT GCC AAG ACA AAG CCG CGG GAG GAG CAG TAC

N   S   T   Y   R   V   V   S   V   L   T   V   L   H   Q   D   W   L   N   G
AAC AGC ACG TAC CGT GTG GTC AGC GTC CTC ACC GTC CTG CAC CAG GAC TGG CTG AAT GGC

K   E   Y   K   C   K   V   S   N   K   A   L   P   A   P   I   E   K   T   I
AAG GAG TAC AAG TGC AAG GTC TCC AAC AAA GCC CTC CCA GCC CCC ATC GAG AAA ACC ATC

S   K   A   K   G   Q   P   R   E   P   Q   V   Y   T   L   P   P   S   R   D
TCC AAA GCC AAA GGG CAG CCC CGA GAA CCA CAG GTG TAC ACC CTG CCC CCA TCC CGG GAT

E   L   T   K   N   Q   V   S   L   T   C   L   V   K   G   F   Y   P   S   D
GAG CTG ACC AAG AAC CAG GTC AGC CTG ACC TGC CTG GTC AAA GGC TTC TAT CCC AGC GAC

I   A   V   E   W   E   S   N   G   Q   P   E   N   N   Y   K   T   T   P   P
ATC GCC GTG GAG TGG GAG AGC AAT GGG CAG CCG GAG AAC AAC TAC AAG ACC ACG CCT CCC

V   L   D   S   D   G   S   F   F   L   Y   S   K   L   T   V   D   K   S   R
GTG CTG GAC TCC GAC GGC TCC TTC TTC CTC TAC AGC AAG CTC ACC GTG GAC AAG AGC AGG

W   Q   Q   G   N   V   F   S   C   S   V   M   H   E   A   L   H   N   H   Y
TGG CAG CAG GGG AAC GTC TTC TCA TGC TCC GTG ATG CAT GAG GCT CTG CAC AAC CAC TAC

T   Q   K   S   L   S   L   S   P   G   K
ACG CAG AAG AGC CTC TCC CTG TCT CCG GGT AAA
```

In one embodiment, the antibodies described supra further comprise a heavy chain constant region, wherein the heavy chain constant region comprises a γ1, γ2, γ3, or γ4 human heavy chain constant region or a variant thereof. In one embodiment, the antibodies described above further comprise a light chain constant region, wherein the light chain constant region comprises a lambda or a kappa human light chain constant region. In some embodiments, the binding fragment of these antibodies is an antibody fragment selected from the group consisting of Fab, Fab', Fab'-SH, Fv, scFv, F(ab')$_2$, and a diabody.

Also provided herein is a chimeric recombinant antibody molecule that binds IL-10 or binding fragment thereof, comprising: at least one antibody light chain variable region, or binding fragment thereof, comprising a polypeptide having at least one amino acid sequence selected from the group consisting of SEQ ID NO:1 at CDR1, SEQ ID NO:2 at CDR2, and SEQ ID NO:3 at CDR3; and at least one antibody heavy chain variable region, or binding fragment thereof, comprising a polypeptide having at least one amino acid sequence selected from the group consisting of SEQ ID NO:6 at CDR1, SEQ ID NO:7 at CDR2, and SEQ ID NO:8 at CDR3.

In a specific embodiment, the chimeric recombinant antibody molecule has a light chain as set forth in SEQ ID NO: 23 and a heavy chain as set forth in SEQ ID NO:24. See Table 8. Nucleic acids encoding the 12G8 chimeric antibody light and heavy chains were deposited at the ATCC as deposit numbers PTA-5925 and PTA-5924, respectively.

TABLE 8

Sequences of the chimeric 12G8 anti-human IL-10 antibody

SEQ ID NO: 23 Amino acid sequence of light chain
SEQ ID NO: 25 Nucleic acid sequence of light chain

```
-->signal sequence
 M   A   P   V   Q   L   L   G   L   L   V   L   F   L   P   A   M   R   C
ATG GCT CCA GTT CAA CTT TTA GGG CTT TTG GTG CTC TTC CTC CCA GCC ATG AGA TGT
mature IgG
-->rat 12G8 light variable domain
 D   I   Q   M   T   Q   S   P   S   L   L   S   A   S   V   G   D   R   V   T   L   N
GAC ATC CAG ATG ACC CAG TCT CCT TCA CTC CTG TCT GCA TCT GTG GGA GAC AGA GTC ACT CTC AAC C   K   T   S   Q   N   I   F   E   N   L   A   W   Y   Q   Q   K   L   R   E   P   P
TGC AAG ACA AGT CAG AAC ATT TTT GAG AAC TTG GCC TGG TAT CAG CAA AAG CTT AGA GAA CCT CCC K   L   L   I   F   N   A   S   P   L   Q   A   G   I   P   S   R   F   S   G   S   G
AAA CTC CTG ATT TTT AAT GCA AGC CCT TTG CAA GCG GGC ATC CCT TCA AGG TTC AGT GGC AGT GGA S   G   T   D   F   T   L   T   I   T   S   L   Q   P   E   D   V   A   T   Y   F   C
TCT GGT ACA GAT TTC ACA CTC ACC ATC ACC AGC CTG CAG CCT GAG GAT GTT GCC ACA TAT TTC TGC -->human
 H   Q   Y   Y   S   G   Y   T   F   G   P   G   T   K   L   E   L   K   R   T   V   A
CAC CAG TAT TAT AGC GGG TAC ACG TTT GGA CCT GGG ACC AAG CTG GAA CTG AAA CGT ACG GTG GCT constant light domain
 A   P   S   V   F   I   F   P   P   S   D   E   Q   L   K   S   G   T   A   S   V   V
GCA CCA TCT GTC TTC ATC TTC CCG CCA TCT GAT GAG CAG TTG AAA TCT GGA ACT GCC TCT GTT GTG C   L   L   N   N   F   Y   P   R   E   A   K   V   Q   W   K   V   D   N   A   L   Q
TGC CTG CTG AAT AAC TTC TAT CCC AGA GAG GCC AAA GTA CAG TGG AAG GTG GAT AAC GCC CTC CAA S   G   N   S   Q   E   S   V   T   E   Q   D   S   K   D   S   T   Y   S   L   S   S
TCG GGT AAC TCC CAG GAG AGT GTC ACA GAG CAG GAC AGC AAG GAC AGC ACC TAC AGC CTC AGC AGC T   L   T   L   S   K   A   D   Y   E   K   H   K   V   Y   A   C   E   V   T   H   Q
ACC CTG ACG CTG AGC AAA GCA GAC TAC GAG AAA CAC AAA GTC TAC GCC TGC GAA GTC ACC CAT CAG G   L   S   S   P   V   T   K   S   F   N   R   G   E   C
GGC CTG AGC TCG CCC GTC ACA AAG AGC TTC AAC AGG GGA GAG TGT TAA
```

SEQ ID NO: 24 Amino acid sequence of heavy chain
SEQ ID NO: 26 Nucleic acid sequence of heavy chain

```
 M   D   I   R   L   S   L   V   F   L   V   L   F   M   K   D   V   Q   C
ATG GAC ATC AGG CTC AGC TTG GTT TTC CTT GTC CTT TTT ATG AAA GAT GTC CAG TGT mature IgG
--> rat 12G8 variable heavy domain
 E   V   Q   L   V   E   S   G   G   G   L   V   R   P   G   G   S   L   R   L   S   C
GAG GTG CAG TTG GTG GAG TCT GGA GGA GGC TTG GTG CGG CCT GGA GGG TCC CTG AGA CTC TCC TGT T   A   S   G   F   T   F   S   D   Y   H   M   A   W   V   R   Q   S   P   D   K   G
ACA GCC TCA GGA TTC ACT TTC AGT GAC TAT CAC ATG GCC TGG GTC CGC CAG TCT CCA GAC AAG GGT L   E   W   V   A   S   I   T   L   D   A   T   Y   T   Y   Y   R   D   S   V   R   G
CTG GAG TGG GTC GCA AGC ATT ACT CTT GAT GCT ACC TAC ACT TAC TAT CGC GAC TCC GTG AGG GGC R   F   T   I   S   R   N   N   A   K   T   T   L   Y   L   Q   M   D   S   L   R   S
CGA TTC ACC ATC TCC CGA AAT AAT GCA AAA ACC ACC CTT TAC CTG CAA ATG GAC AGT CTG AGG TCT
```

TABLE 8-continued

Sequences of the chimeric 12G8 anti-human IL-10 antibody

| E | D | T | A | T | F | Y | C | T | R | H | R | G | F | S | V | W | L | D | Y | W | G |
|---|---|---|---|---|---|---|---|---|---|---|---|---|---|---|---|---|---|---|---|---|---|
| GAG | GAC | ACG | GCC | ACT | TTT | TAC | TGT | ACA | AGA | CAT | CGA | GGC | TTT | AGC | GTC | TGG | CTT | GAT | TAC | TGG | GGC |

-->human IgG1 heavy chain

| Q | G | V | M | V | T | V | S | S | A | S | T | K | G | P | S | V | F | P | L | A | P |
|---|---|---|---|---|---|---|---|---|---|---|---|---|---|---|---|---|---|---|---|---|---|
| CAA | GGA | GTC | ATG | GTC | ACT | GTC | TCT | TCA | GCT | AGC | ACC | AAG | GGC | CCA | TCG | GTC | TTC | CCC | CTG | GCA | CCC |

| S | S | K | S | T | S | G | G | T | A | A | L | G | C | L | V | K | D | Y | F | P | E |
|---|---|---|---|---|---|---|---|---|---|---|---|---|---|---|---|---|---|---|---|---|---|
| TCC | TCC | AAG | AGC | ACC | TCT | GGG | GGC | ACA | GCG | GCC | CTG | GGC | TGC | CTG | GTC | AAG | GAC | TAC | TTC | CCC | GAA |

| P | V | T | V | S | W | N | S | G | A | L | T | S | G | V | H | T | F | P | A | V | L |
|---|---|---|---|---|---|---|---|---|---|---|---|---|---|---|---|---|---|---|---|---|---|
| CCG | GTG | ACG | GTG | TCG | TGG | AAC | TCA | GGC | GCC | CTG | ACC | AGC | GGC | GTG | CAC | ACC | TTC | CCG | GCT | GTC | CTA |

| Q | S | S | G | L | Y | S | L | S | S | V | V | T | V | P | S | S | S | L | G | T | Q |
|---|---|---|---|---|---|---|---|---|---|---|---|---|---|---|---|---|---|---|---|---|---|
| CAG | TCC | TCA | GGA | CTC | TAC | TCC | CTC | AGC | AGC | GTG | GTG | ACC | GTG | CCC | TCC | AGC | AGC | TTG | GGC | ACC | CAG |

| T | Y | I | C | N | V | N | H | K | P | S | N | T | K | V | D | K | K | V | E | P | K |
|---|---|---|---|---|---|---|---|---|---|---|---|---|---|---|---|---|---|---|---|---|---|
| ACC | TAC | ATC | TGC | AAC | GTG | AAT | CAC | AAG | CCC | AGC | AAC | ACC | AAG | GTG | GAC | AAG | AAA | GTT | GAG | CCC | AAA |

| S | C | D | K | T | H | T | C | P | P | C | P | A | P | E | L | L | G | G | P | S | V |
|---|---|---|---|---|---|---|---|---|---|---|---|---|---|---|---|---|---|---|---|---|---|
| TCT | TGT | GAC | AAA | ACT | CAC | ACA | TGC | CCA | CCG | TGC | CCA | GCA | CCT | GAA | CTC | CTG | GGG | GGA | CCG | TCA | GTC |

| F | L | F | P | P | K | P | K | D | T | L | M | I | S | R | T | P | E | V | T | C | V |
|---|---|---|---|---|---|---|---|---|---|---|---|---|---|---|---|---|---|---|---|---|---|
| TTC | CTC | TTC | CCC | CCA | AAA | CCC | AAG | GAC | ACC | CTC | ATG | ATC | TCC | CGG | ACC | CCT | GAG | GTC | ACA | TGC | GTG |

| V | V | D | V | S | H | E | D | P | E | V | K | F | N | W | Y | V | D | G | V | E | V |
|---|---|---|---|---|---|---|---|---|---|---|---|---|---|---|---|---|---|---|---|---|---|
| GTG | GTG | GAC | GTG | AGC | CAC | GAA | GAC | CCT | GAG | GTC | AAG | TTC | AAC | TGG | TAC | GTG | GAC | GGC | GTG | GAG | GTG |

| H | N | A | K | T | K | P | R | E | E | Q | Y | N | S | T | Y | R | V | V | S | V | L |
|---|---|---|---|---|---|---|---|---|---|---|---|---|---|---|---|---|---|---|---|---|---|
| CAT | AAT | GCC | AAG | ACA | AAG | CCG | CGG | GAG | GAG | CAG | TAC | AAC | AGC | ACG | TAC | CGT | GTG | GTC | AGC | GTC | CTC |

| T | V | L | H | Q | D | W | L | N | G | K | E | Y | K | C | K | V | S | N | K | A | L |
|---|---|---|---|---|---|---|---|---|---|---|---|---|---|---|---|---|---|---|---|---|---|
| ACC | GTC | CTG | CAC | CAG | GAC | TGG | CTG | AAT | GGC | AAG | GAG | TAC | AAG | TGC | AAG | GTC | TCC | AAC | AAA | GCC | CTC |

| P | A | P | I | E | K | T | I | S | K | A | K | G | Q | P | R | E | P | Q | V | Y | T |
|---|---|---|---|---|---|---|---|---|---|---|---|---|---|---|---|---|---|---|---|---|---|
| CCA | GCC | CCC | ATC | GAG | AAA | ACC | ATC | TCC | AAA | GCC | AAA | GGG | CAG | CCC | CGA | GAA | CCA | CAG | GTG | TAC | ACC |

Further provided herein is a chimeric recombinant antibody molecule that binds IL-10, or binding fragment thereof, comprising: at least one antibody light chain, or binding fragment thereof, comprising a polypeptide having at least one amino acid sequence selected from the group consisting of SEQ ID NO:11 at CDR1, SEQ ID NO:12 at CDR2, and SEQ ID NO:13 at CDR3; and at least one antibody heavy chain, or binding fragment thereof, comprising a polypeptide having at least one amino acid sequence selected from the group consisting of SEQ ID NO:15 at CDR1, SEQ ID NO:16 at CDR2, and SEQ ID NO:17 at CDR3.

Further provided herein is an isolated nucleic acid encoding the polypeptide of the antibodies disclosed supra. Also provided herein is an expression vector comprising the isolated nucleic acid sequence operably linked to control sequences recognized by a host cell transfected with the vector. Provided herein is a host cell comprising the vector comprising the isolated nucleic acid sequence. Further provided herein is a method of producing a polypeptide, comprising culturing the host cell comprising the vector under conditions wherein the nucleic acid sequence is expressed, thereby producing the polypeptide, and recovering the polypeptide from the host cell.

Provided herein is an isolated nucleic acid sequence encoding an antibody specific for IL-10 comprising a light chain having the nucleic acid sequence of SEQ ID NO:19 and a heavy chain having the nucleic acid sequence of SEQ ID NO:20. See Tables 4 and 5.

Provided herein is an isolated nucleic acid sequence encoding an antibody specific for IL-10 comprising a light chain having the nucleic acid sequence of SEQ ID NO:21 and a heavy chain having the nucleic acid sequence of SEQ ID NO:22. See Tables 6 and 7.

Further provided herein is an isolated nucleic acid sequence encoding a binding fragment of the antibody encoded by the above nucleic acid sequences. In one embodiment, the binding fragment is an antibody fragment selected from the group consisting of Fab, Fab', Fab'-SH, Fv, scFv, F(ab')$_2$, and a diabody.

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305: 537-39 (1983). Alternatively, bispecific antibodies can be prepared using chemical linkage. See, e.g., Brennan, et al., Science 229: 81 (1985). Bispecific antibodies include bispecific antibody fragments. See, e.g., Hollinger, et al., Proc. Natl. Acad. Sci. U.S.A. 90: 6444-48 (1993), Gruber, et al., J. Immunol. 152: 5368 (1994).

D. BIOLOGICAL ACTIVITY OF HUMANIZED ANTI-IL-10 ANTIBODIES

Antibodies having the characteristics identified herein as being desirable in a humanized anti-IL-10 antibody can be screened for inhibitory biologic activity in vitro or suitable binding affinity. To screen for antibodies which bind to the epitope on human IL-10 bound by an antibody of interest (e.g., those which block binding of the cytokine to its receptor), a routine cross-blocking assay such as that described in ANTIBODIES, A LABORATORY MANUAL, Cold Spring Harbor Laboratory, Ed Harlow and David Lane (1988), can be performed. Alternatively, epitope mapping, e.g., as described in Champe et al., *J. Biol. Chem.* 270: 1388-1394 (1995), can be performed to determine whether the antibody binds an epitope of interest. Antibody affinities (e.g. for human IL-10) may be determined using standard Scatchard analysis. Preferred humanized antibodies are those which bind human IL-10 with a $K_d$ value of no more than about $1 \times 10^{-7}$; preferably no more than about $1 \times 10^{-8}$; more preferably no more than about $1 \times 10^{-9}$; and most preferably no more than about $2 \times 10^{-10}$.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of IL-10 to bind its receptor. As used herein, the term "specific" refers to the selective binding of the antibody to the target antigen epitope. Antibodies can be tested for specificity of binding by comparing binding to IL-10 to binding to irrelevant antigen or antigen mixture under a given set of conditions. If the antibody binds to IL-10 at least 10, and preferably 50 times more than to irrelevant antigen or antigen mixture then it is considered to be specific.

The inhibitory IL-10 specific antibody can inhibit its biological activity in any manner, including but not limited to production of IL-1, IFN-γ, PGE2, IL-12, TNF, CC and CXC chemokines, and the cell surface expression of MHC class II antigens, CD54, CD80, and CD86. The biologic activity of an IL-10 specific antibody can be determined by any useful method. See, e.g., U.S. Pat. Nos. 6,239,260 and 6,207,154. In one example, the biologic activity is assessed in cell proliferation assay using the murine mast cell line, MC9/2. See Thompson-Snipes et al., *J. Exp. Med.* 173:507-10 (1991). IL-10 stimulates the proliferation of this cell line, and therefore an inhibitory antibody can be identified by its ability to reduce proliferation. The $ED_{50}$ for proliferation of the MC9/2 cell line is typically 0.5-1.0 ng/mL. An antibody is inhibitory for proliferation if it inhibits the proliferation of cells relative to the proliferation of cells in the absence of the antibody or in the presence of a non-binding antibody. Proliferation may be quantified using any suitable methods. Typically, the proliferation is determined by assessing the incorporation of radioactive-labeled nucleotides into DNA (e.g., $^3$H-thymidine). In another embodiment, proliferation is determined by ATP luminescence. Preferably, the antibody useful in the present compositions inhibits 80% of IL-10's biologic activity, more preferably 95%, most preferably 99%.

E. USES OF HUMANIZED ANTI-IL-10 ANTIBODIES

Provided herein is a method of suppressing an immune response in a human subject comprising administering to a subject in need thereof an antibody specific for IL-10, or a binding fragment thereof, in an amount effective to block the biological activity of IL-10, wherein the antibody is a humanized recombinant antibody molecule that binds IL-10, or binding fragment thereof, comprising: at least one antibody light chain variable region, or binding fragment thereof, comprising a polypeptide having at least one amino acid sequence selected from the group consisting of SEQ ID NO:1 at CDR1, SEQ ID NO:2 at CDR2, and SEQ ID NO:3 at CDR3; and a framework region, wherein the amino acid sequence of framework region is all or substantially all of a human immunoglobin amino acid sequence; and at least one antibody heavy chain variable region, or binding fragment thereof, comprising a polypeptide having at least one amino acid sequence selected from the group consisting of SEQ ID NO:6 at CDR1, SEQ ID NO:7 at CDR2, and SEQ ID NO:8 at CDR3; and a framework region, wherein the amino acid sequence of framework region is all or substantially all of a human immunoglobin amino acid sequence.

Further provided herein is a method of suppressing an immune response in a human subject comprising administering to a subject in need thereof an antibody specific for IL-10, or a binding fragment thereof, in an amount effective to block the biological activity of IL-10, wherein the antibody is a humanized recombinant antibody molecule that binds IL-10, or binding fragment thereof, comprising: at least one antibody light chain, or binding fragment thereof, comprising a polypeptide having at least one amino acid sequence selected from the group consisting of SEQ ID NO:11 at CDR1, SEQ ID NO:12 at CDR2, and SEQ ID NO:13 at CDR3; and a framework region, wherein the amino acid sequence of framework region is all or substantially all of a human immunoglobin amino acid sequence; and at least one antibody heavy chain, or binding fragment thereof, comprising a polypeptide having at least one amino acid sequence selected from the group consisting of SEQ ID NO:15 at CDR1, SEQ ID NO:16 at CDR2, and SEQ ID NO:17 at CDR3; and a framework region, wherein the amino acid sequence of framework region is all or substantially all of a human immunoglobin amino acid sequence.

The immune response suppressed by these methods is a humoral or a cellular response. The suppression of the humoral and cellular responses can be determined using well known methods in the art. For example, in diseases associated with high levels of autoreactive antibodies, e.g., SLE, a reduction in the serum levels of these antibodies relative to the pre-treatment serum levels is an indication of the suppression of the humoral response. Likewise, the suppression of the cellular immune response can be determined using well known in vitro analyses, e.g., proliferation and cytotoxicity assays or characterization of activation phenotypes of peripheral blood lymphocytes by, e.g., flow cytometric analysis. See CURRENT PROTOCOLS IN IMMUNOLOGY, most recent edition. In one embodiment, the subject treated by this method has systemic lupus erythematosus. In another embodiment, the subject has immune thrombocytopenic purpura (ITC). In yet another embodiment, the subject has lupus nephritis. In a further embodiment, the subject has HIV. In another embodiment, the subject has hepatitis C.

Provided herein is a composition comprising an antibody, or binding fragment thereof, in combination with a pharmaceutically acceptable carrier or diluent, wherein the antibody is one of the antibodies disclosed herein.

Any subject that would benefit from treatment with IL-10 specific antibodies can be treated using the compositions and methods provided herein. Any subject can be treated with the methods and compositions provided herein. Such a subject is a mammal, preferably a human, with an autoimmune disease or symptom or pathogen-induced immunopathology. In one specific embodiment, the subject has SLE, lupus nephritis, rheumatoid arthritis, ITC, HIV or hepatitis C. Veterinary uses of the disclosed methods and compositions are also contemplated.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an IL-10 specific antibody that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

An antibody useful in the present methods (from whatever source derived, including without limitation from recombinant and non-recombinant sources) may be administered to a subject in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

In another embodiment, kits are provided that contain the necessary reagents to carry out the assays of the methods provided herein. Specifically provided herein is a compartment kit comprising one or more containers, wherein a first container comprises one or more antibodies specific to IL-10, and one or more other containers comprising one or more of the following: reconstitution reagents, administration reagents. The containers can be glass, plastic, or strips of plastic or paper. In one embodiment, the kit also contain written instructions.

In practicing the methods of treatment or use provided herein, a therapeutically effective amount of antibody provided herein is administered to a mammal having a condition suitable for treatment with IL-10. The antibody may be administered in accordance with the methods herein either alone or in combination with other therapies such as treatments employing other immunomodulating factors (e.g., cytokines), immunosuppressive agents, and the like. When co-administered with one or more biologically active agents, the antibody provided herein may be administered either simultaneously with the biologically active agent(s), or sequentially. If administered sequentially, the attending physician will decide on the appropriate sequence of administering protein of the present invention in combination with the biologically active agent(s).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

Techniques for formulation and administration of the antibodies of the instant methods may be found in REMINGTON'S PHARMACEUTICAL SCIENCES, Mack Publishing Co., Easton, Pa., latest edition. The mode of administration is not particularly important. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. Intravenous administration to the patient is preferred.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Pharmaceutical compositions for use in accordance with the present methods thus may be formulated in a conventional manner using one or more physiologically acceptable carriers comprising excipients and auxiliaries that facilitate processing of the active compounds into preparations that can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of antibody of the methods herein is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For administration by inhalation, the antibodies for use according to the present methods are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

The amount of antibody useful in the disclosed methods in the pharmaceutical composition of the present invention will depend upon the nature and severity of the condition being treated, and on the nature of prior treatments that the patient has undergone. Ultimately, the attending physician will decide the amount of protein of the present invention with which to treat each individual patient. It is to be expected that the dosage will vary according to the age, weight and response of the individual patient. Initially, the attending physician will administer low doses of antibodies of the present methods and observe the patient's response. Larger doses of antibodies of the present invention may be administered until the optimal therapeutic effect is obtained for the patient, and at that point the dosage is not increased further. It is contemplated that the various pharmaceutical compositions used to practice the methods herein should contain about 0.01 µg to about 100 mg (preferably about 0.1 µg to about 10 mg, more preferably about 0.1 µg to about 1 mg) of antibody of the present invention per kg body weight. When administered, the therapeutic composition for use in this invention is, of course, in a pyrogen-free, physiologically acceptable form. Therapeutically useful agents other than an antibody of the present methods that may also optionally be included in the composition as described above, may alternatively or additionally, be administered simultaneously or sequentially with the composition in the methods of the invention. The exact formulation, route of administration and dosage can be chosen by the individual physician in view of the patient's condition. See, e.g., Fingl et al., THE PHARMACOLOGICAL BASIS OF THERAPEUTICS (latest edition). Dosage amount and interval may be adjusted individually to provide plasma levels of the active moiety sufficient to maintain the desired therapeutic effects, or minimal effective concentration (MEC). The MEC will vary for each compound but can be estimated from in vitro data; for example, the concentration necessary to achieve 50-90% inhibition of biologic activity using the assays described herein.

The antibody provided herein can be administered alone or in combination with other therapeutic modalities. The antibody provided herein also can be administered alone or in combination with other antibodies identified as inhibitors of IL-10 activity or other immunosuppressive agents.

Any disease where autoimmunity is implicated can be treated with the present methods. Preferably, autoimmune diseases targeted for treatment with IL-10 specific antibodies are characterized by abnormal IL-10 expression levels and/or a lack of appropriate cellular, i.e., Th1-mediated, responses. Such disease include, but are not limited to systemic lupus erythematosus (SLE), immune thrombocytopenic purpura (ITC), lupus nephritis, diabetes, insulin-dependent diabetes mellitus (IDDM), rheumatoid arthritis (RA).

Any disease where pathogen-induced immunopathology is implicated can be treated with the present methods. Preferably, pathogen-induced immunopathologies targeted for treatment with IL-10 specific antibodies are characterized by abnormal IL-10 expression levels and/or a lack of appropriate cellular, i.e., Th1-mediated, responses. Such diseases include, but are not limited to HIV, hepatitis C, visceral leishmaniasis, malaria, filariasis, leprosy, tuberculosis, candidiasis, and M. avium infections.

The broad scope of this invention is best understood with reference to the following examples, which are not intended to limit the inventions to the specific embodiments.

F. EXAMPLES

Example I

General Methods

Some of the standard methods are described or referenced, e.g., in Maniatis, et al. (1982) MOLECULAR CLONING, A LABORATORY MANUAL, Cold Spring Harbor Laboratory, Cold Spring Harbor Press; Sambrook, et al. (1989) MOLECULAR CLONING: A LABORATORY MANUAL, (2d ed.), vols. 1-3, CSH Press, NY; Ausubel, et al., BIOLOGY, Greene Publishing Associates, Brooklyn, N.Y.; or Ausubel, et al. (1987 and Supplements) CURRENT PROTOCOLS IN MOLECULAR BIOLOGY, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in METH. ENZYMOL., vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1990) "Purification of Recombinant Proteins with Metal Chelate Absorbent" in Setlow (ed.) GENETIC ENGINEERING, PRINCIPLE AND METHODS 12:87-98, Plenum Press, N.Y.; and Crowe, et al. (1992) QIAEXPRESS: THE HIGH LEVEL EXPRESSION & PROTEIN PURIFICATION SYSTEM, Qiagen, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Example II

Humanization of Anti-Human IL-10 Antibodies

The humanization of the rat anti-human IL-10 antibody, 12G8, was performed as described in Section C supra. FIG. 1 shows the assignment of the assignment of residue numbers and corresponding numerical scores for residue positions that are identical to the germline sequences being examined. Calculations are shown for the 12G8 variable regions of the light (FIG. 1A) and heavy (FIG. 1B) of the 12G8 anti-human IL-10 antibody and for the variable regions of the light (FIG. 1C) and heavy (FIG. 1D) of the 11D8 anti-human IL-10 antibody.

Example III

Pharmacokinetics of 12G8, an Anti-Human IL-10 Antibody

Objective:
To obtain estimates of in-vivo terminal half-lives and subcutaneous bioavailability for the 12F8 antibody in a murine model.

Antibody:
The antibody is administered in a vehicle of 10 mM Na acetate, 8% sucrose, pH 5.25.

Mice:
Crl:CD-1® (ICR) BR female mice were purchased from Charles River Laboratories.

Experimental Design:
Mice received a single bolus injection of antibody either intravenously (i.v. in lateral tail vein) or subcutaneously (s.c. at nape of neck or mid-scapular or lateral flank). Antibody doses included 0.03, 0.3, 3.0, and 30 mg/kg per mouse. The mice were observed for up to 28 days post-injection. During this time period, mice were weighed and serum samples taken. Serum samples for the 12G8 (SCH 708980) groups (Groups 1-8) were taken at 0.5, 1, 3, 6, 10, 16 hrs, Day 1, 2, 3, 5, 7, 10, 14, 21, and 28 post-injection using 5 mice/time point. In the vehicle group (Group 9), serum samples were taken at pre-injection, 1 hr post-injection, 14 day or 21 day only using 5 mice/time point. Serum IL-10 levels and serum 12G8 antibody levels were determined using specific ELISAs.

Pharmacokinetic Parameter Determinations.
All parameters were estimated or calculated using WinNonlin Pro v 4.0. For noncompartmental analyses, Model 200 (SC) or Model 201 (IV) was used. Input data were dose-normalized group arithmetic mean concentration-time data. Input doses were nominal doses for Groups 2-4 and 6-8. Input dose for Groups 1 and 5 was 0.014 mg/kg. For compartmental analyses, Model 3 (SC) or Model 7 (IV) was used. Input data were dose-normalized individual animal concentration-time data. All fits used uniform weighting (wt=1) for individual data points. Input doses were nominal doses for Groups 2-4 and 6-8. Input dose for Groups 1 and 5 was 0.014 mg/kg. Good of fit was evaluated using visual inspection, comparisons of SE's for estimated/calculated parameters, residuals, and AIC & SBC criteria.

A summary of the dosing solution recovery is shown in the Table below.

TABLE 9

Summary of Body Weights, Dose Levels, and Dosing Solution Concentrations (mean ± SD

| Group | Route | Body Weights (g) | Nominal Dose Level[B] (mg/kg) | Actual Dose Level (mg/kg) | Nominal Dosing Soln Conc[D] (mg/mL) | Actual Dosing Soln Conc (mg/mL) | Actual Dose % of Nominal |
|---|---|---|---|---|---|---|---|
| 1 | IV | 28.2 ± 2.61 | 0.03 | 11.4 ± 1.02 | ~0.0075 | 0.0032 | 38.0 |
| 2 | IV | 29.7 ± 2.83 | 0.3 | 251 ± 23.4 | ~0.075 | 0.074 | 83.7 |
| 3 | IV | 24.5 ± 2.00 | 3.0 | 3410 ± 268 | ~0.75 | 0.83 | 114 |
| 4 | IV | 30.0 ± 3.38 | 30.0 | 28300 ± 3040 | Min 7.5 | 8.40 | 94.3 |
| 5 | SC | 28.4 ± 2.38 | 0.03 | 11.4 ± 0.954 | ~0.0075 | 0.0032 | 38.0 |
| 6 | SC | 29.9 ± 2.87 | 0.3 | 250 ± 23.1 | ~0.075 | 0.074 | 83.3 |
| 7 | SC | 24.7 ± 1.95 | 3.0 | 3380 ± 263 | ~0.75 | 0.83 | 113 |
| 8 | SC | 29.7 ± 2.61 | 30.0 | 28500 ± 248 | Min 7.5 | 8.4 | 95.0 |

The tables shown below summarize the data from the groups receiving the 12G8 antibody via i.v. injection.

TABLE 10

Noncompartmental Method Parameters for IV Bolus Dosing Groups

| | | Parameters | | | | |
|---|---|---|---|---|---|---|
| Group (fold incr) | Dose Level (mg/kg) | $AUC_{0\text{-}last}$ (day*ug/mL) | $V_z$ (mL/kg) | CL (mL/day/kg) | Initial $t_{1/2}$ (day) | Term $t_{1/2}$ (day) |
| 1 | 0.014 | 1.97 | 87.3 | 4.68 | NC | 12.9 |
| 2 (21.4x) | 0.3 | 44.1 (22.3x) | 99.6 | 5.08 | NC | 13.6 |
| 3 (10x) | 3.0 | 404 (9.2x) | 127 | 5.08 | NC | 17.3 |
| 4 (10x) | 30 | 4000 (9.9x) | 101 | 6.36 | NC | 11.0 |

TABLE 11

Compartmental Method Parameters for IV Bolus Dosing Groups

| | | Parameters | | | | |
|---|---|---|---|---|---|---|
| Group (fold incr) | Dose Level (mg/kg) | $AUC_{0\text{-}inf}$ (day*ug/mL) | $V_i$ (mL/kg) | CL (mL/day/kg) | Initial $t_{1/2}$ (day) | Term $t_{1/2}$ (day) |
| 1 | 0.014 | 2.22 | 31.4 | 5.13 | 0.041 | 10.5 |
| 2 (21.4x) | 0.3 | 53.5 (24.1x) | 48.7 | 5.60 | 0.105 | 11.6 |
| 3 (10x) | 3.0 | 550 (10.3x) | 55.7 | 5.46 | 0.103 | 15.0 |
| 4 (10x) | 30 | 4500 (8.18) | 45.8 | 6.67 | 0.08 | 9.79 |

The tables shown below summarize the data from the groups receiving the 12F8 antibody via s.c. injection.

TABLE 12

Noncompartmental Method Parameters for SC Bolus Dosing Groups

| | | Parameters | | | | | |
|---|---|---|---|---|---|---|---|
| Group (fold incr) | Dose Level (mg/kg) | $AUC_{0\text{-}last}$ (day*ug/mL) | $C_{max}$ (ug/mL) | $T_{max}$ (day) | F (%) | $T_{1/2}$ abs (day) | $T_{1/2}$ elim (day) |
| 1 | 0.03 | 1.56 | 0.113 | 2.0 | 77.8 | NC | 18.9 |
| 2 (21.4x) | 0.3 | 44.9 (28.8x) | 3.56 (31.5x) | 0.417 | 100 | NC | 13.0 |
| 3 (10x) | 3.0 | 343 (7.6x) | 24.4 (6.85x) | 1.00 | 84.8 | NC | 13.6 |
| 4 (10x) | 30 | 3170 (9.2x) | 247 (10.1x) | 0.667 | 79.3 | NC | 8.76 |

* Bioavailability may be high due to underestimating IV AUC.

TABLE 13

Compartmental Method Parameters for SC Bolus Dosing Groups

| | | Parameters | | | | | |
|---|---|---|---|---|---|---|---|
| Group (fold incr) | Dose Level (mg/kg) | $AUC_{0\text{-}last}$ (day*ug/mL) | $C_{max}$ (ug/mL) | $T_{max}$ (day) | F (%) | $t_{1/2}$ abs (day) | $t_{1/2}$ elim (day) |
| 1 | 0.03 | 2.00 | 0.107 | 1.44 | 90.0 | 0.254 | 11.9 |
| 2 (21.4x) | 0.3 | 53.5 (26.8x) | 3.11 (29.1x) | 1.31 | 100 | 0.229 | 11.0 |
| 3 (10x) | 3.0 | 450 (8.41x) | 22.4 (7.20x) | 1.59 | 81.7 | 0.284 | 12.7 |
| 4 (10x) | 30 | 3210 (7.1x) | 256 (11.4x) | 1.25 | 71.3 | 0.241 | 7.78 |

Concentration-time profiles are shown for 12F8 antibody using various dosages and routes in FIG. 2.

Conclusions:

The doses were within 20% of nominal for all groups except lowest dose level. Lower than expected concentrations, probably due to presence of anti-SCH708980 (humanized 12G8) antibodies were observed from Day 10 post-injection in groups 7 or 8. (A) IV Bolus Pharmacokinetics. Half-lives, clearance and distribution volumes are typical of those seen for other IgG1 monoclonal antibodies. Distribution volume is approximately equal to or slightly larger than serum volume suggesting minimal extravascular distribution. The terminal half-lives ranged from 10 to 17 days. The increase in AUC was generally dose-proportional suggesting linear PK over the dose range tested. (B) SC Bolus Pharmacokinetics. The maximum concentrations were generally dose-proportional and were reached by 1-2 days postdose suggesting consistent rates and extents of absorption over the dose range tested. The increase in AUC was generally dose-proportional suggesting linear PK. The terminal elimination half-lives ranged from 8-14 days, similar to other IgG1 monoclonal antibodies. The absolute bioavailability was high, range=70-100%, although the estimates>90% may be high due to underestimation of IV AUC.

Example IV

Determining the Equilibrium Dissociation Constant (Kd) for Humanized Anti-Human IL-10 Antibody SCH 708980 (12G8) using KinExA Technology The equilibrium dissociation constant (Kd) for humanized antibody SCH 708980 was determined using KinExA 3000 (Sapidyne Instruments Inc.). KinExA uses the principle of the Kinetic Exclusion Assay method based on measuring the concentration of uncomplexed antibody in a mixture of antibody, antigen and antibody-antigen complex. The concentration of free antibody was measured by exposing the mixture to a solid-phase immobilized antigen for a very brief period of time. In practice, this was accomplished by flowing the solution phase antigen-antibody mixture past antigen coated particles trapped in a flow cell. Data generated by the instrument were analyzed using custom software. Equilibrium constants were calculated using a mathematical theory based on the following assumptions:

1. The binding follows the reversible binding equation for equilibrium:

$$K_{on}[Ab][Ag] = K_{off}[AbAg]$$

2. Antibody and antigen bind 1:1, and total antibody equals antigen-antibody complex plus free antibody
3. Instrument signal is linearly related to free antibody concentration Materials Used:

Monoclonal humanized antibody SCH 708980 to recombinant human IL-10 (h12G8); recombinant human IL-10 (hIL-10); recombinant mouse IL-10 (mIL-10), recombinant cyno IL-10 (cyno IL-10); PMMA particles, 98 micron (Sapidyne, Cat No. 440198); Neutravidin (Pierce, Cat No. 31000); EZ-link TFP PEO-Biotin (Pierce, Cat No. 21219); Biotinylated rhIL-10; and Cy5 conjugated Goat anti-HuIgG (H+L) (Jackson Immunoresearch Laboratories Cat. No 109-175-088, lot 49069).

PMMA particles were coated with biotinylated rhIL5 according to manufacturer's protocols. For biotinylation of rhIL5 EZ-link TFP PEO-biotin was used according to manufacturer's recommendations (Pierce bulletin 0874). All experimental procedures were done according to the KinExA 3000 manual.

Experimental Conditions:

All runs were done in duplicate. For hIL-10 runs the following conditions were used:
Sample volume: 1.5 ml
Sample flow rate: 0.25 ml/min
Label volume: 0.5 ml
Label flow rate: 0.25 ml/min
mAb conc.: 0.1 nM
Highest Ag (hIL-10) conc.: 4.0 nM
Lowest Ag (hIL-10) conc.: 3.91 pM Two-fold serial dilutions of the antigen were prepared and mixed with the antibody at constant concentration. The mixture was incubated for 2 hours at room temperature (RT) to equilibrate.

For mIL-10 runs the following conditions were used:
Sample volume: 0.5 ml
Sample flow rate: 0.25 ml/min
Label volume: 0.5 ml
Label flow rate: 0.25 ml/min
mAb conc.: 1 nM
Highest Ag (mIL-10) conc.: 50 nM
Lowest Ag (mIL-10) conc.: 48.8 pM Two-fold serial dilutions of the antigen were prepared and mixed with the antibody at constant concentration. The mixture was incubated for 2 hours at RT. to equilibrate.

For cyno IL-10 runs the following conditions were used:
Sample volume: 2 ml
Sample flow rate: 0.25 ml/min
Label volume: 1 ml
Label flow rate: 0.25 ml/min
mAb conc.: 0.1 nM
Highest Ag (mIL-10) conc.: 5.0 nM
Lowest Ag (mIL-10) conc.: 4.88 pM Two-fold serial dilutions of the antigen were prepared and mixed with the antibody at constant concentration. The mixture was incubated for 2 hours at RT to equilibrate.

The results are shown in the Table below.

TABLE 14

Equilibrium Dissociation constant (Kd) for 12F8 Antibody using KinExA technology

| Antigen | Antigen monomer M. W. (kDa) | Antibody | Kd (Standard) | Error (%) |
|---|---|---|---|---|
| hIL-10 #1 | 19.5 | hz × hIL-10 mAb 12G8-1 | 2.738e−11 | 2.18% |
| hIL-10 #2 | 19.5 | hz × hIL-10 mAb 12G8, SCH708980 | 3.232e−11 | 4.4% |
| hIL-10 #3 | 19.5 | hz × hIL-10 mAb 12G8, SCH708980 | 1.553e−11 | 3.7% |
| mIL-10 #1 | 19.5 | hz × hIL-10 mAb 12G8-1 | 2.82e−10 | 1.42% |
| mIL-10 #2 | 19.5 | hz × hIL-10 mAb 12G8, SCH708980 | 2.673e−10 | 1.65% |
| mIL-10 #3 | 19.5 | hz × hIL-10 mAb 12G8, SCH708980 | 3.078e−10 | 1.97% |
| Cyno IL-10 #1 | 19.5 | hz × hIL-10 mAb 12G8-1 | 3.97e−11 | 1.93% |
| Cyno IL-10 #2 | 19.5 | hz × hIL-10 mAb 12G8, SCH708980 | 9.657e−11 | 1.37% |
| Cyno IL-10 #3 | 19.5 | hz × hIL-10 mAb 12G8, SCH708980 | 9.245e−11 | 3.5% |

Example V

Application of Competitive Electrochemiluminescence Assay (ECLA) to Measure Binding of Anti-hIL-10 Monoclonal Antibodies and hIL-10-Ra to Recombinant IL-10 of Different Origin Summary of Technology.

Electrochemiluminescence technology was developed by IGEN, Inc (Gaithersburg, Md.) and is employed in the M-series M8/384 analyzer used in this work. Electrochemiluminescence technology utilizes a stable ruthenium metal chelate (Ori-TAG) which, in the presence of tripropylamine (TPA), generates electrochemiluminescence upon voltage application. Paramagnetic beads, microns in diameter, act as the solid phase and facilitate rapid assay kinetics. The bead/complex is channeled through a flow cell and captured at an electrode by magnetic application. Voltage is applied and resulting electrochemiluminescence is measured.

Materials Used.

96 well Polypropylene plates (Costar, Cat. No. 3365, Fisher Sci. Cat. No. 07200697); assay buffer of 0.1% BSA, 0.05% tween 20, PBS pH 7.5; paramagnetic beads (Streptavidin-Dynabeads, Igen, Inc., Cat. No. 110029); recombinant human IL-10 dimer (hIL-10-dimer); recombinant human IL-10-monomer (hIL-10-mono); recombinant mouse IL-10 (mIL-10); recombinant cyno IL-10 (cyno IL-10); and recombinant hIL-10Ra (hIL-10Ra): FLAG-tagged protein. Ori-Tag labeled anti-FLAG M2 monoclonal antibodies were prepared using Ori-Tag-NHS ester (Igen, Inc. Cat. No. 110034) according to manufacturer's protocol (OriTag label: IgG challenge ratio 8:1). Anti-Flag M2 monoclonal antibodies were purchased from Sigma (Cat. No. F3165). Ori-Tag labeled anti hIgG 1A2 monoclonal antibodies were prepared as above using rat anti hIgG monoclonal antibodies. Ori-Tag labeled anti rat IgG antibodies were prepared as above from polyclonal Goat anti rat IgG (H+L) antibodies (Jackson Immunoresearch Laboratories, Inc. PA, Cat. No. 112-005-143). Biotinylated recombinant human IL-10 (hIL-10-biotin) was prepared using TFP-PEO-biotin (Pierce, Cat. No. 21219) according to manufacturer's recommenda tions (Pierce bulletin 0874). The rat anti hIL-10 mAb 12G8 (r12G8): JES3.12G8 and humanized anti hIL-10 mAb 12G8 (h12G8-1) were prepared as described herein.

Protocol.

1/3 serial dilutions in 50 microliters of the assay buffer were made in 96-well microtiter plate for all unlabeled IL-10 preparations (mIL-10, cyno IL-10, hIL-10 dimer, hIL-10 mono) starting with 3 µg/ml in the first well. All samples were run in duplicates. 50 µl of hIL-10-biotin at 25 ng/ml was added to each well, followed by the addition of either hIL-10Ra (50 µl at 100 ng/ml) or anti hIL-10 mAb (50 µl at 10 ng/ml). 50 microliters of Ori-Tag conjugated secondary antibodies was added to each well at 500 ng/ml conc. For hIL-10Ra, r12G8 and h12G8 the following Ori-Tag conjugated were used accordingly: anti-FLAG M2-OriTag, anti-rat IgG-OriTag and anti hIgG 1A2-OriTag. Finally to each well 50 µl of Streptavidin-Dynabeads at 0.1 mg/ml was added. After a one hour incubation at room temperature the plate was processed by the M-series M8/384 analyzer. Percent inhibition of the signal by unlabeled IL-10 preparations was calculated relative to the control samples. To plot the data and calculate $IC_{50}$ the GraphPad Prism Software was used.

Results are shown in the Table below.

TABLE 15

| Binding affinity determination using ECLA | | | | |
|---|---|---|---|---|
| Antigen | Antigen monomer M. W. (kDa) | Antibody/Receptor | $IC_{50}$(nM) | SD |
| mIL-10 | 19.5 | Rat × hIL-10 mAb JES3.12G8 | 37.9 | 17.8 |
| Cyno IL-10 | 19.5 | Rat × hIL-10 mAb JES3.12G8 | 6.6 | 1.5 |
| hIL-10 (dimer) | 19.5 | Rat × hIL-10 mAb JES3.12G8 | 4.7 | 0.8 |
| hIL-10 (monomer) | 19.5 | Rat × hIL-10 mAb JES3.12G8 | 7.1 | 0.6 |
| mIL-10 | 19.5 | hz × hIL-10 mAb 12G8-1 | 53.0 | 8.2 |
| Cyno IL-10 | 19.5 | hz × hIL-10 mAb 12G8-1 | 4.9 | 0.9 |
| hIL-10 (dimer) | 19.5 | hz × hIL-10 mAb 12G8-1 | 4.0 | 0.5 |
| hIL-10 (monomer) | 19.5 | hz × hIL-10 mAb 12G8-1 | 5.8 | 1.0 |
| mIL-10 | 19.5 | huIL-10Ra | no binding | — |
| Cyno IL-10 | 19.5 | huIL-10Ra | 17.6 | 7.0 |
| hIL-10 (dimer) | 19.5 | huIL-10Ra | 2.9 | 0.4 |
| hIL-10 (monomer) | 19.5 | huIL-10Ra | 7.2 | 1.1 |

The results of the characterization of the rat 12G8 antibody and the humanized 12G8 antibody (SCH708980) are summarized in the Table below.

TABLE 16

| | IGEN $IC_{50}$(nM) mean ± S.D. (n) | Kinexa Kd(pM) mean ± S.D.(n) | Biacore Kd(pM) mean ± S.D.(n) | Bioassay $IC_{50}$(pM) mean ± S.D.(n) |
|---|---|---|---|---|
| Rat 12G8 | | | | |
| mouse IL-10 | 38 ± 18 (2) | | 7400 ± 2500 (9) | |
| cyno IL-10 | 6.6 ± 1.5 (2) | | 330 ± 60 (9) | |
| hu IL-10 | 4.7 ± 0.8 (2) | 23 (1) | 277 ± 39 (7) | 66 ± 9 (5) |
| SCH708980 (hu12G8) | | | | |
| mouse IL-10 | 53 ± 8 (2) | 286 ± 21 (3) | 8600 ± 600 (8) | |
| cyno IL-10 | 4.9 ± 0.9 (2) | 76 ± 32 (3) | 659 ± 71 (8) | |
| hu IL-10 | 4.0 ± 0.5 (2) | 25 ± 9 (3) | 511 ± 68 (11) | 93 ± 9 (5) |

Example VI

Neutralizing Effects of Humanized Anti-Human IL-10 Antibody In Vivo

Figure 3B:
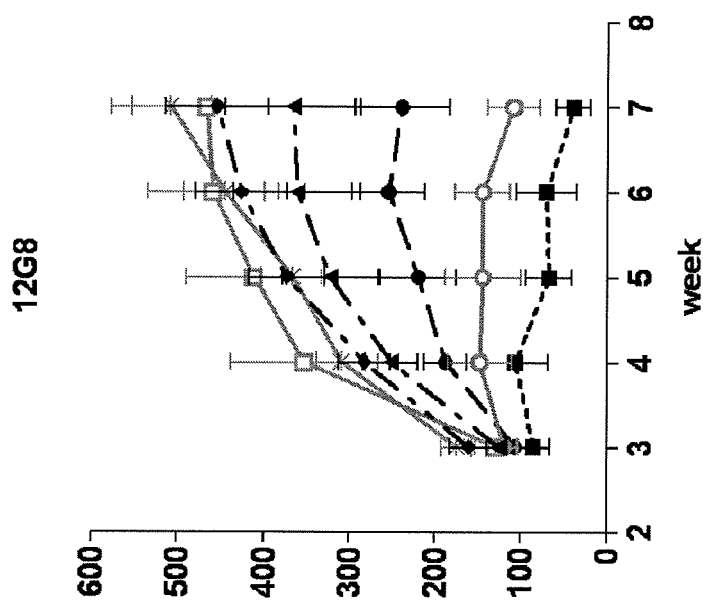
FIG. 3B shows that administration of the rat anti-IL-10 antibody, 12G8, confers resistance to Leishmania major infection in IL-10 transgenic mice. Infection was determined by measuring footpad swelling with a caliper at the times indicated. 12G8 antibody was administered as described in Example VI.

In vivo neutralizing efficacy of SCH 708980 and JES.12G8 was evaluated in the *Leishmania major* model in mice. In this model, CB6F1 mice normally resistant to parasite infection were rendered susceptible by heterozygosity for a human IL-10 transgene under the control of the MHC class II promoter. CB6F1 or CB6F1-huIL-10Tg mice were injected s.c. with SCH 708980 or JES.12G8 weekly beginning three days before s.c. footpad challenge with $15 \times 10^6$ stationary phase *L. major* parasites. Disease progression was monitored by weekly measurements of footpad swelling. FIG. 3 shows that both SCH708980 (the humanized 12G8) and the parental rat 12G8 neutralized the protective effect of IL-10 in a dose-dependent manner.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

The invention claimed is:

1. An isolated nucleic acid sequence encoding a humanized antibody, or antigen binding fragment thereof, that binds IL-10, wherein the humanized antibody or antigen binding fragment thereof comprises:
   a) at least one light chain variable region having the amino acid sequence of SEQ ID NO: 4; or
   b) at least one heavy chain variable region having the amino acid sequence of SEQ ID NO: 9.

2. An expression vector comprising the isolated nucleic acid of claim 1 operably linked to control sequences recognized by a host cell transfected with the vector.

3. A host cell comprising the vector of claim 2.

4. The nucleic acid of claim 1, wherein the light chain comprises the nucleic acid sequence of SEQ ID NO: 19 and the heavy chain comprises the nucleic acid sequence of SEQ ID NO: 20.

5. An expression vector comprising the nucleic acid of claim 4 operably linked to control sequences recognized by a host cell transfected with the vector.

6. A host cell comprising the vector of claim 5.

7. The nucleic acid of claim 1, wherein the antigen binding fragment is selected from the group consisting of a Fab, Fab', Fab'-SH, Fv, sc-Fv, F(ab)2 and a diabody.

* * * * *

```
                              SEQUENCE LISTING

<160> NUMBER OF SEQ ID NOS: 38

<210> SEQ ID NO 1
<211> LENGTH: 11
<212> TYPE: PRT
<213> ORGANISM: Rattus norvegicus

<400> SEQUENCE: 1

Lys Thr Ser Gln Asn Ile Phe Glu Asn Leu Ala
1               5                   10

<210> SEQ ID NO 2
<211> LENGTH: 7
<212> TYPE: PRT
<213> ORGANISM: Rattus norvegicus

<400> SEQUENCE: 2

Asn Ala Ser Pro Leu Gln Ala
1               5

<210> SEQ ID NO 3
<211> LENGTH: 8
<212> TYPE: PRT
<213> ORGANISM: Rattus norvegicus

<400> SEQUENCE: 3

His Gln Tyr Tyr Ser Gly Tyr Thr
1               5

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Phe Glu Asn
            20                  25                  30

Leu Ala Trp Tyr Gln Gln Lys Pro Gly Lys Ala Pro Lys Leu Leu Ile
        35                  40                  45

Tyr Asn Ala Ser Pro Leu Gln Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Ser Gly Tyr Thr
                85                  90                  95

Phe Gly Pro Gly Thr Lys Leu Glu Leu Lys Arg Thr
            100                 105

<210> SEQ ID NO 5
<211> LENGTH: 213
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asn Ile Phe Glu Asn
            20                  25                  30
```

```
Leu Ala Trp Tyr Gln Gln Lys Pro Gly Lys Ala Pro Lys Leu Leu Ile
         35                  40                  45

Tyr Asn Ala Ser Pro Leu Gln Ala Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Tyr Ser Gly Tyr Thr
                 85                  90                  95

Phe Gly Pro Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210
```

<210> SEQ ID NO 6
<211> LENGTH: 10
<212> TYPE: PRT
<213> ORGANISM: Rattus norvegicus

<400> SEQUENCE: 6

```
Gly Phe Thr Phe Ser Asp Tyr His Met Ala
 1               5                  10
```

<210> SEQ ID NO 7
<211> LENGTH: 17
<212> TYPE: PRT
<213> ORGANISM: Rattus norvegicus

<400> SEQUENCE: 7

```
Ser Ile Thr Leu Asp Ala Thr Tyr Thr Tyr Tyr Arg Asp Ser Val Arg
 1               5                  10                  15

Gly
```

<210> SEQ ID NO 8
<211> LENGTH: 10
<212> TYPE: PRT
<213> ORGANISM: Rattus norvegicus

<400> SEQUENCE: 8

```
His Arg Gly Phe Ser Val Trp Leu Asp Tyr
 1               5                  10
```

<210> SEQ ID NO 9
<211> LENGTH: 119
<212> TYPE: PRT
<213> ORGANISM: Homo sapiens

<400> SEQUENCE: 9

```
Gln Val Gln Leu Val Glu Ser Gly Gly Gly Val Val Gln Pro Gly Arg
```

```
                 1               5              10              15

Ser Leu Arg Leu Ser Cys Ala Ala Ser Gly Phe Thr Phe Ser Asp Tyr
                     20                  25                  30

His Met Ala Trp Val Arg Gln Ala Pro Gly Lys Gly Leu Glu Trp Val
                     35                  40                  45

Ala Ser Ile Thr Leu Asp Ala Thr Tyr Thr Tyr Tyr Arg Asp Ser Val
                 50                  55                  60

Arg Gly Arg Phe Thr Ile Ser Arg Asp Asn Ser Lys Asn Thr Leu Tyr
          65                  70                  75                  80

Leu Gln Met Asn Ser Leu Arg Ala Glu Asp Thr Ala Val Tyr Tyr Cys
                             85                  90                  95

Ala Arg His Arg Gly Phe Ser Val Trp Leu Asp Tyr Trp Gly Gln Gly
                        100                 105                 110

Thr Leu Val Thr Val Ser Ser
                        115

<210> SEQ ID NO 10
         <211> LENGTH: 449
         <212> TYPE: PRT
         <213> ORGANISM: Homo sapiens

<400> SEQUENCE: 10

Gln Val Gln Leu Val Glu Ser Gly Gly Gly Val Val Gln Pro Gly Arg
         1               5                  10                  15

Ser Leu Arg Leu Ser Cys Ala Ala Ser Gly Phe Thr Phe Ser Asp Tyr
                     20                  25                  30

His Met Ala Trp Val Arg Gln Ala Pro Gly Lys Gly Leu Glu Trp Val
                     35                  40                  45

Ala Ser Ile Thr Leu Asp Ala Thr Tyr Thr Tyr Tyr Arg Asp Ser Val
                 50                  55                  60

Arg Gly Arg Phe Thr Ile Ser Arg Asp Asn Ser Lys Asn Thr Leu Tyr
          65                  70                  75                  80

Leu Gln Met Asn Ser Leu Arg Ala Glu Asp Thr Ala Val Tyr Tyr Cys
                             85                  90                  95

Ala Arg His Arg Gly Phe Ser Val Trp Leu Asp Tyr Trp Gly Gln Gly
                        100                 105                 110

Thr Leu Val Thr Val Ser Ser Ala Ser Thr Lys Gly Pro Ser Val Phe
                        115                 120                 125

Pro Leu Ala Pro Ser Ser Lys Ser Thr Ser Gly Gly Thr Ala Ala Leu
             130                 135                 140

Gly Cys Leu Val Lys Asp Tyr Phe Pro Glu Pro Val Thr Val Ser Trp
         145                 150                 155                 160

Asn Ser Gly Ala Leu Thr Ser Gly Val His Thr Phe Pro Ala Val Leu
                         165                 170                 175

Gln Ser Ser Gly Leu Tyr Ser Leu Ser Ser Val Val Thr Val Pro Ser
                     180                 185                 190

Ser Ser Leu Gly Thr Gln Thr Tyr Ile Cys Asn Val Asn His Lys Pro
                 195                 200                 205

Ser Asn Thr Lys Val Asp Lys Lys Val Glu Pro Lys Ser Cys Asp Lys
             210                 215                 220

Thr His Thr Cys Pro Pro Cys Pro Ala Pro Glu Leu Leu Gly Gly Pro
         225                 230                 235                 240

Ser Val Phe Leu Phe Pro Pro Lys Pro Lys Asp Thr Leu Met Ile Ser
                         245                 250                 255

Arg Thr Pro Glu Val Thr Cys Val Val Val Asp Val Ser His Glu Asp
```

```
                        260                 265                 270
Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 11
<211> LENGTH: 15
<212> TYPE: PRT
<213> ORGANISM: Rattus norvegicus

<400> SEQUENCE: 11

Arg Ala Ser Glu Ser Val Asp Asp Tyr Gly His Ser Phe Met His
1               5                   10                  15

<210> SEQ ID NO 12
<211> LENGTH: 7
<212> TYPE: PRT
<213> ORGANISM: Rattus norvegicus

<400> SEQUENCE: 12

Arg Ala Ser Thr Leu Glu Ser
1               5

<210> SEQ ID NO 13
<211> LENGTH: 9
<212> TYPE: PRT
<213> ORGANISM: Rattus norvegicus

<400> SEQUENCE: 13

Gln Gln Gly Asn Glu Asp Pro Trp Thr
1               5

<210> SEQ ID NO 14
<211> LENGTH: 218
<212> TYPE: PRT
<213> ORGANISM: Homo sapiens

<400> SEQUENCE: 14

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Glu Ser Val Asp Asp Tyr
             20                  25                  30
Gly His Ser Phe Met His Trp Tyr Gln Gln Lys Pro Gly Gln Ala Pro
         35                  40                  45
Arg Leu Leu Ile Tyr Arg Ala Ser Thr Leu Glu Ser Gly Ile Pro Asp
 50                  55                  60
Arg Phe Ser Gly Ser Gly Ser Gly Thr Asp Phe Thr Leu Thr Ile Ser
 65                  70                  75                  80
Arg Leu Glu Pro Glu Asp Phe Ala Val Tyr Tyr Cys Gln Gln Gly Asn
                 85                  90                  95
Glu Asp Pro Trp Thr Phe Gly Gln Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
210                 215

<210> SEQ ID NO 15
<211> LENGTH: 10
<212> TYPE: PRT
<213> ORGANISM: Rattus norvegicus

<400> SEQUENCE: 15

Gly Phe Ser Leu Thr Asn Tyr Gly Val His
1               5                   10

<210> SEQ ID NO 16
<211> LENGTH: 16
<212> TYPE: PRT
<213> ORGANISM: Rattus norvegicus

<400> SEQUENCE: 16

Val Ile Trp Ser Gly Gly Ser Thr Asp Tyr Asn Ala Ala Phe Ile Ser
1               5                   10                  15

<210> SEQ ID NO 17
<211> LENGTH: 10
<212> TYPE: PRT
<213> ORGANISM: Rattus norvegicus

<400> SEQUENCE: 17

Asn Arg Gly Tyr Asp Val Tyr Phe Asp Tyr
1               5                   10

<210> SEQ ID NO 18
<211> LENGTH: 448
<212> TYPE: PRT
<213> ORGANISM: Homo sapiens

<400> SEQUENCE: 18
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
            35                  40                  45

Ala Val Ile Trp Ser Gly Gly Ser Thr Asp Tyr Asn Ala Ala Phe Ile
50                      55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Arg Gly Tyr Asp Val Tyr Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

420              425              430
Leu His Asn His Tyr Thr Gln Lys Ser Leu Ser Leu Ser Pro Gly Lys
          435              440              445

<210> SEQ ID NO 19
<211> LENGTH: 639
<212> TYPE: DNA
<213> ORGANISM: Homo sapiens

<400> SEQUENCE: 19
gacatccaga tgacccagtc tccatcctcc ctgtctgcat ctgtaggaga cagagtcacc      60
atcacttgca agacaagtca gaacattttt gagaacttgg cctggtatca gcagaaacca     120
gggaaagccc ctaagctcct gatctataat gcaagccctt tgcaagcggg ggtcccatca     180
aggttcagtg gcagtggatc tgggacagat ttcactctca ccatcagcag tctgcaacct     240
gaagattttg caacttacta ctgtcaccag tattatagcg gtacacgtt tggacctggg      300
accaagctgg aactgaaacg tacgtggct gcaccatctg tcttcatctt cccgccatct      360
gatgagcagt tgaaatctgg aactgcctct gttgtgtgcc tgctgaataa cttctatccc     420
agagaggcca agtacagtg gaaggtggat aacgccctcc aatcgggtaa ctcccaggag      480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639

<210> SEQ ID NO 20
<211> LENGTH: 1347
<212> TYPE: DNA
<213> ORGANISM: Homo sapiens

<400> SEQUENCE: 20
caggtgcagc tggtggagtc tgggggaggc gtggtccagc ctgggaggtc cctgagactc      60
tcctgtgcag cctctggatt cactttcagt gactatcata tggcctgggt ccgccaggct     120
ccaggcaagg ggctggagtg ggtggcaagc attactcttg atgctaccta cacttactat     180
cgcgactccg tgcgcggccg cttcaccatc tccagagaca attccaagaa cacgctgtat     240
ctgcaaatga acagcctgag agctgaggac acggctgtgt attactgtgc gagacatcga     300
ggctttagcg tctggcttga ttactgggc caaggcaccc tggtcaccgt ctcgtcggct      360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatccag cgacatcgcc    1140

```
gtggagtggg agagcaatgg gcagccggag aacaactaca agaccacgcc tcccgtgctg        1200
gactccgacg gctccttctt cctctacagc aagctcaccg tggacaagag caggtggcag        1260
caggggaacg tcttctcatg ctccgtgatg catgaggctc tgcacaacca ctacacgcag        1320
aagagcctct ccctgtctcc gggtaaa                                            1347

<210> SEQ ID NO 21
<211> LENGTH: 654
<212> TYPE: DNA
<213> ORGANISM: Homo sapiens

<400> SEQUENCE: 21
gaaattgtgt tgacgcagtc tccaggcacc ctgtctttgt ctccagggga aagagccacc          60
ctctcctgca gagccagtga aagtgttgat gattatggcc atagttttat gcactggtac         120
cagcagaaac ctggccaggc tcccaggctc ctcatctatc gtgcatccac cctagaatct         180
ggcatcccag acaggttcag tggcagtggg tctgggacag acttcactct caccatcagc         240
agactggagc ctgaagattt tgcagtgtat tactgtcagc aaggtaatga ggatccgtgg         300
acgttcggtc aaggtaccaa ggtggaaatc aagcgtacgg tggctgcacc atctgtcttc         360
atcttcccgc catctgatga gcagttgaaa tctggaactg cctctgttgt gtgcctgctg         420 ataacttct atcccagaga ggccaaagta cagtggaagg tggataacgc cctccaatcg          480
ggtaactccc aggagagtgt cacagagcag gacagcaagg acagcaccta cagcctcagc         540
agcaccctga cgctgagcaa agcagactac gagaaacaca agtctacgc ctgcgaagtc          600 acccatcagg gcctgagctc gcccgtcaca aagagcttca caggggaga gtgt                654

<210> SEQ ID NO 22
<211> LENGTH: 1344
<212> TYPE: DNA
<213> ORGANISM: Homo sapiens

<400> SEQUENCE: 22
caggtgcagc tggtggagtc tgggggaggc gtggtccagc ctgggaggtc cctgagactc          60
tcctgtgcag cctctggttt tcattaaca aactatggtg tacactgggt ccgccaggct         120
ccaggcaagg ggctggagtg ggtggcagtg atatggagtg gtggaagcac agactataat         180
gcagctttca tatcccgatt caccatctcc agagacaatt ccaagaacac gctgtatctg         240
caaatgaaca gcctgagagc tgaggacacg gctgtgtatt actgtgcgag aaataggggg         300
tacgacgtct actttgacta ctggggccaa ggcacccttg tcacagtctc gtcggctagc         360
accaagggcc catcggtctt ccccctggca ccctcctcca agagcacctc tgggggcaca         420
gcggccctgg gctgcctggt caaggactac ttccccgaac cggtgacggt gtcgtggaac         480
tcaggcgccc tgaccagcgg cgtgcacacc ttcccggctg tcctacagtc ctcaggactc         540
tactccctca gcagcgtggt gaccgtgccc tccagcagct gggcaccca gacctacatc          600 tgcaacgtga atcacaagcc cagcaacacc aaggtggaca gaaagttga gcccaaatct          660 tgtgacaaaa ctcacacatg cccaccgtgc ccagcacctg aactcctggg gggaccgtca         720
gtcttcctct tccccccaaa acccaaggac accctcatga tctcccggac ccctgaggtc         780
acatgcgtgg tggtggacgt gagccacgaa gaccctgagg tcaagttcaa ctggtacgtg         840
gacggcgtgg aggtgcataa tgccaagaca aagccgcggg aggagcagta caacagcacg         900
taccgtgtgg tcagcgtcct caccgtcctg caccaggact ggctgaatgg caaggagtac         960
aagtgcaagg tctccaacaa agccctccca gcccccatcg agaaaaccat ctccaaagcc        1020
```

```
aaagggcagc ccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                          1344
```

<210> SEQ ID NO 23
<211> LENGTH: 232
<212> TYPE: PRT
<213> ORGANISM: Artificial
<220> FEATURE:
<223> OTHER INFORMATION: Chimeric 12G8

<400> SEQUENCE: 23

```
Met Ala Pro Val Gln Leu Leu Gly Leu Leu Val Leu Phe Leu Pro Ala
1               5                   10                  15

Met Arg Cys Asp Ile Gln Met Thr Gln Ser Pro Ser Leu Leu Ser Ala
            20                  25                  30

Ser Val Gly Asp Arg Val Thr Leu Asn Cys Lys Thr Ser Gln Asn Ile
        35                  40                  45

Phe Glu Asn Leu Ala Trp Tyr Gln Gln Lys Leu Arg Glu Pro Pro Lys
    50                  55                  60

Leu Leu Ile Phe Asn Ala Ser Pro Leu Gln Ala Gly Ile Pro Ser Arg
65                  70                  75                  80

Phe Ser Gly Ser Gly Ser Gly Thr Asp Phe Thr Leu Thr Ile Thr Ser
                85                  90                  95

Leu Gln Pro Glu Asp Val Ala Thr Tyr Phe Cys His Gln Tyr Tyr Ser
            100                 105                 110

Gly Tyr Thr Phe Gly Pro Gly Thr Lys Leu Glu Leu Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 24
<211> LENGTH: 371
<212> TYPE: PRT
<213> ORGANISM: Artificial
<220> FEATURE:
<223> OTHER INFORMATION: Chimeric 12G8

<400> SEQUENCE: 24

```
Met Asp Ile Arg Leu Ser Leu Val Phe Leu Val Leu Phe Met Lys Asp
1               5                   10                  15
```

Val Gln Cys Glu Val Gln Leu Val Glu Ser Gly Gly Leu Val Arg
        20                  25                  30

Pro Gly Gly Ser Leu Arg Leu Ser Cys Thr Ala Ser Gly Phe Thr Phe
            35                  40                  45

Ser Asp Tyr His Met Ala Trp Val Arg Gln Ser Pro Asp Lys Gly Leu
    50                  55                  60

Glu Trp Val Ala Ser Ile Thr Leu Asp Ala Thr Tyr Thr Tyr Tyr Arg
65                  70                  75                  80

Asp Ser Val Arg Gly Arg Phe Thr Ile Ser Arg Asn Asn Ala Lys Thr
                85                  90                  95

Thr Leu Tyr Leu Gln Met Asp Ser Leu Arg Ser Glu Asp Thr Ala Thr
            100                 105                 110

Phe Tyr Cys Thr Arg His Arg Gly Phe Ser Val Trp Leu Asp Tyr Trp
        115                 120                 125

Gly Gln Gly Val Met Val Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr
    370

<210> SEQ ID NO 25
<211> LENGTH: 699
<212> TYPE: DNA
<213> ORGANISM: Artificial
<220> FEATURE:
<223> OTHER INFORMATION: Chimeric 12G8

<400> SEQUENCE: 25

```
atggctccag ttcaactttt agggcttttg gtgctcttcc tcccagccat gagatgtgac    60
atccagatga cccagtctcc ttcactcctg tctgcatctg tgggagacag agtcactctc   120
aactgcaaga caagtcagaa catttttgag aacttggcct ggtatcagca aaagcttaga   180
gaacctccca aactcctgat ttttaatgca agcccttgc aagcgggcat cccttcaagg    240
ttcagtggca gtggatctgg tacagatttc acactcacca tcaccagcct gcagcctgag   300
gatgttgcca catatttctg ccaccagtat tatagcgggt acacgtttgg acctgggacc   360
aagctggaac tgaaacgtac ggtggctgca ccatctgtct tcatcttccc gccatctgat   420
gagcagttga atctggaac tgcctctgtt gtgtgcctgc tgaataactt ctatcccaga    480
gaggccaaag tacagtggaa ggtggataac gccctccaat cgggtaactc ccaggagagt   540
gtcacagagc aggacagcaa ggacagcacc tacagcctca gcagcaccct gacgctgagc   600
aaagcagact acgagaaaca caaagtctac gcctgcgaag tcacccatca gggcctgagc   660
tcgcccgtca caaagagctt caacagggga gagtgttaa                          699

<210> SEQ ID NO 26
<211> LENGTH: 1113
<212> TYPE: DNA
<213> ORGANISM: Artificial
<220> FEATURE:
<223> OTHER INFORMATION: Chimeric 12G8

<400> SEQUENCE: 26
atggacatca ggctcagctt ggttttcctt gtccttttta tgaaagatgt ccagtgtgag    60
gtgcagttgg tggagtctgg aggaggcttg gtgcggcctg gagggtccct gagactctcc   120
tgtacagcct caggattcac tttcagtgac atcacatgg cctgggtccg ccagtctcca   180
gacaagggtc tggagtgggt cgcaagcatt actcttgatg ctacctacac ttactatcgc   240
gactccgtga ggggccgatt caccatctcc cgaaataatg caaaaaccac cctttacctg   300
caaatggaca gtctgaggtc tgaggacacg gccactttt actgtacaag acatcgaggc   360
tttagcgtct ggcttgatta ctggggccaa ggagtcatgg tcactgtctc ttcagctagc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc    660 tgcaacgtga atcacaagcc cagcaacacc aaggtggaca gaaagttga gcccaaatct    720 tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac acc                               1113

<210> SEQ ID NO 27
<211> LENGTH: 95
<212> TYPE: PRT
<213> ORGANISM: Homo sapiens

<400> SEQUENCE: 27
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 28
<211> LENGTH: 100
<212> TYPE: PRT
<213> ORGANISM: Homo sapiens

<400> SEQUENCE: 28

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
        100
```

<210> SEQ ID NO 29
<211> LENGTH: 96
<212> TYPE: PRT
<213> ORGANISM: Homo sapiens

<400> SEQUENCE: 29

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 30
<211> LENGTH: 101
<212> TYPE: PRT
<213> ORGANISM: Homo sapiens

<400> SEQUENCE: 30

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100
```

<210> SEQ ID NO 31
<211> LENGTH: 98
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg
```

<210> SEQ ID NO 32
<211> LENGTH: 98
<212> TYPE: PRT
<213> ORGANISM: Homo sapiens

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 33

```
<211> LENGTH: 98
<212> TYPE: PRT
<213> ORGANISM: Homo sapiens

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 34
<211> LENGTH: 98
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 35
<211> LENGTH: 97
<212> TYPE: PRT
<213> ORGANISM: Homo sapiens

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg

<210> SEQ ID NO 36
<211> LENGTH: 98
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Ile Ser Trp Val Arg Gln Ala Pro Gly Gln Gly Leu Glu Trp Met
            35                  40                  45

Gly Trp Ile Asn Pro Gly Asn Gly Asp Thr Asn Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 37
<211> LENGTH: 98
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 38
<211> LENGTH: 96
<212> TYPE: PRT
<213> ORGANISM: Homo sapiens
<220> FEATURE:
<221> NAME/KEY: misc_feature
<222> LOCATION: (57)..(57)
<223> OTHER INFORMATION: Xaa can be any naturally occurring amino acid

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Ser Tyr
                20                  25                  30

Trp Ser Trp Ile Arg Gln Pro Pro Gly Lys Gly Leu Glu Trp Ile Gly
            35                  40                  45

```
Arg Ile Tyr Tyr Ser Gly Ser Thr Xaa Tyr Asn Pro Ser Leu Lys Ser
    50                  55                  60

Arg Val Thr Ile Ser Val Asp Thr Ser Lys Asn Gln Phe Ser Leu Lys
65                  70                  75                  80

Leu Ser Ser Val Thr Ala Ala Asp Thr Ala Val Tyr Tyr Cys Ala Arg
                85                  90                  95
```